United States Patent [19]

Brooks et al.

[11] Patent Number: 4,850,355

[45] Date of Patent: Jul. 25, 1989

[54] HEMOSTATIC CLIP APPLICATOR FOR APPLYING MULTIPLE HEMOSTATIC CLIPS

[75] Inventors: Christopher J. Brooks, Glen Cove, N.Y.; Jeffrey A. Stein, Milford, Conn.; Paul J. Mulhauser, New York, N.Y.

[73] Assignee: Richard-Allan Medical Industries, Inc., Richland, Mich.

[21] Appl. No.: 35,074

[22] Filed: Apr. 6, 1987

[51] Int. Cl.$^4$ .............................................. A61B 17/12
[52] U.S. Cl. ............................. 128/325; 227/DIG. 1
[58] Field of Search ..................... 128/335, 326, 325; 227/144, 140, DIG. 1, DIG. 10

[56] References Cited

U.S. PATENT DOCUMENTS

| | | |
|---|---|---|
| 4,043,504 | 8/1977 | Hueil et al. ................. 227/DIG. 15 |
| 4,152,920 | 5/1979 | Green . |
| 4,242,902 | 1/1981 | Green . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,410,125 | 10/1983 | Noiles et al. ................. 227/DIG. 10 |
| 4,412,539 | 11/1983 | Jarvik . |
| 4,430,997 | 2/1984 | DiGiovanni et al. . |
| 4,452,357 | 6/1984 | Klieman et al. . |
| 4,471,780 | 9/1984 | Menges et al. . |
| 4,478,220 | 10/1984 | DiGiovanni et al. . |
| 4,480,641 | 11/1984 | Failla et al. . |
| 4,509,518 | 4/1985 | McGarry et al. . |
| 4,512,345 | 4/1985 | Green . |
| 4,522,207 | 6/1985 | Klieman et al. . |
| 4,534,351 | 8/1985 | Rothfuss et al. . |
| 4,549,544 | 10/1985 | Favaron . |
| 4,557,263 | 12/1985 | Green . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,674,504 | 6/1987 | Klieman et al. ................. 128/325 |
| 4,691,853 | 9/1987 | Storace ................. 227/DIG. 15 |
| 4,712,549 | 12/1987 | Peters et al. ................. 128/325 |

*Primary Examiner*—John D. Yasko
*Attorney, Agent, or Firm*—Neuman, Williams, Anderson & Olson

[57] ABSTRACT

The present invention relates to an apparatus for applying hemostatic or ligating clips. The apparatus is provided with a unitary chassis on which all other components are attached. A clip housing is disposed at the forward end of the apparatus and stores a plurality of abuttingly arranged forward facing clips that are fed one at a time to the jaws. Upon closure of the handles, the jaws are drawn rearwardly into the apparatus and cammed closed to deform a clip positioned between the jaws. Upon release of the handles, the apparatus returns to its unactuated position and advances a clip to the jaws. The apparatus includes a lockout member to prevent actuation of the apparatus while a clip is in transition from the clip housing to the jaws.

54 Claims, 10 Drawing Sheets

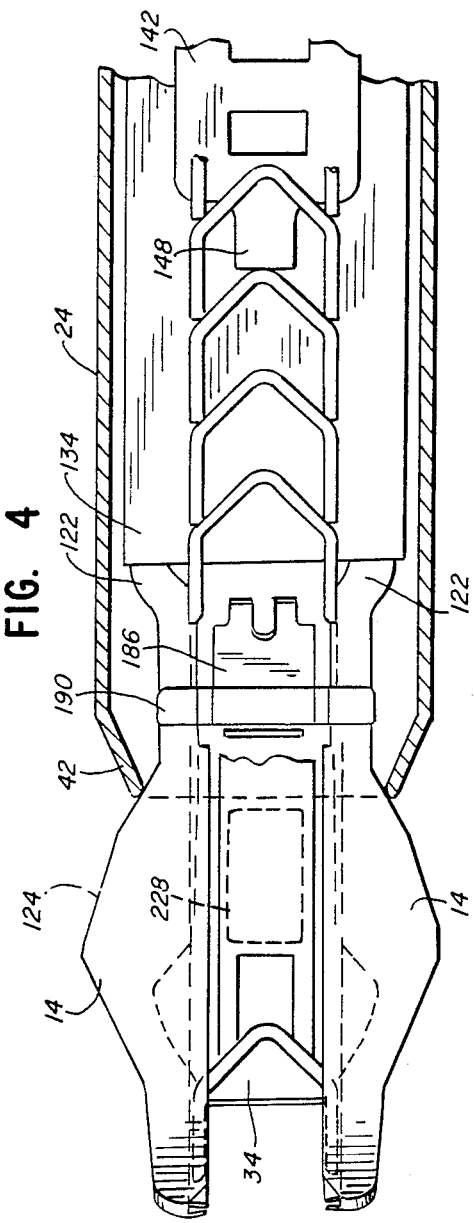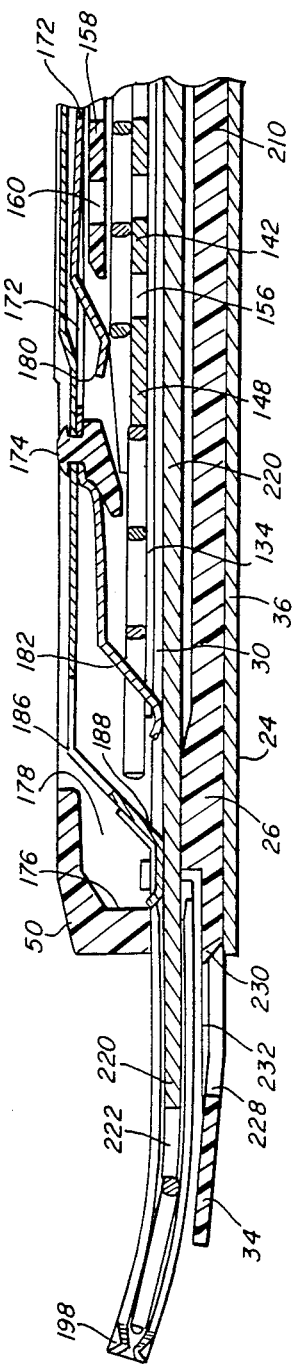

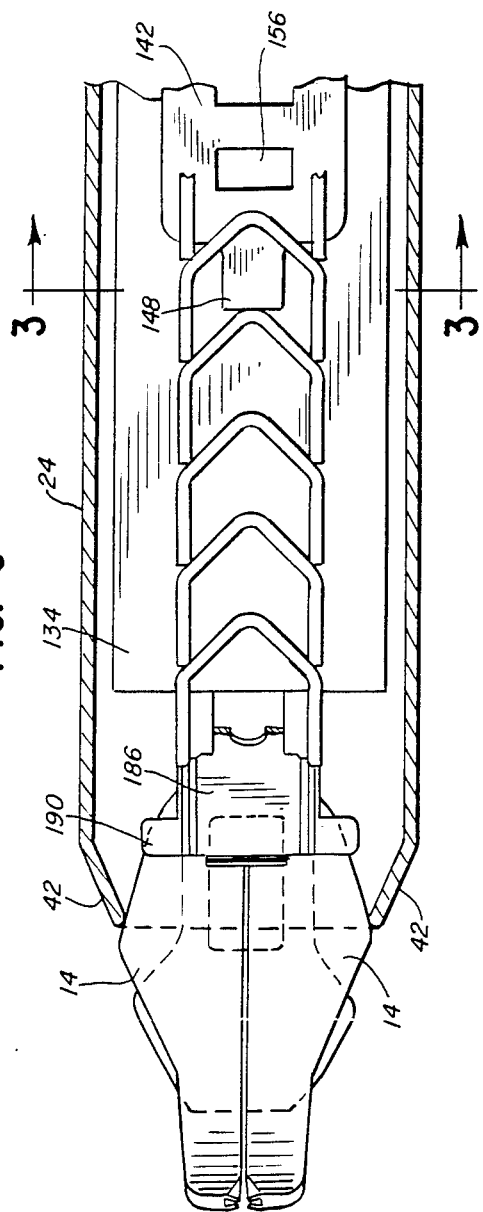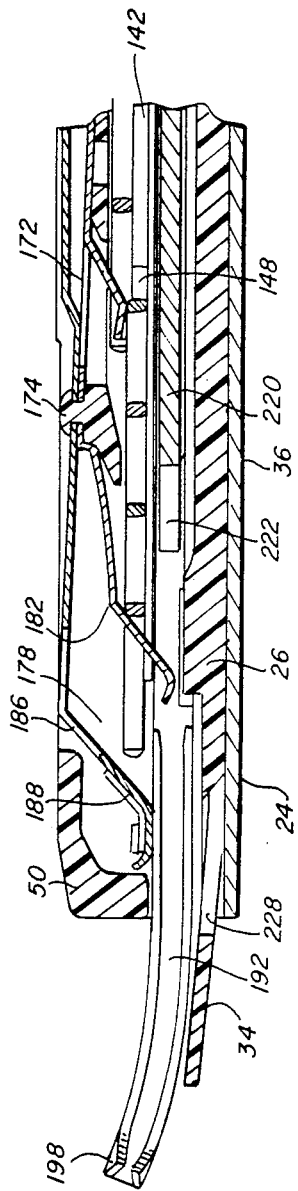
FIG. 6
FIG. 7

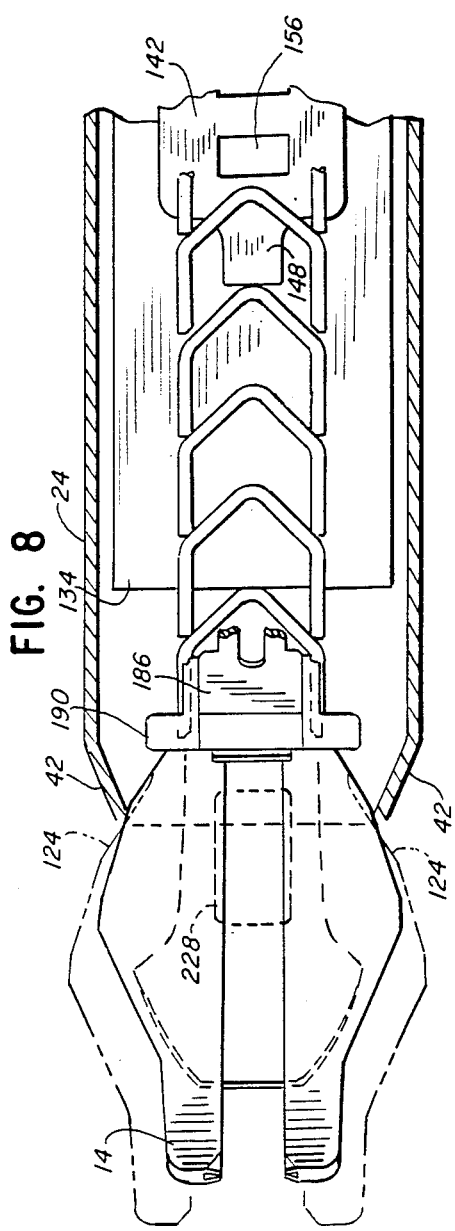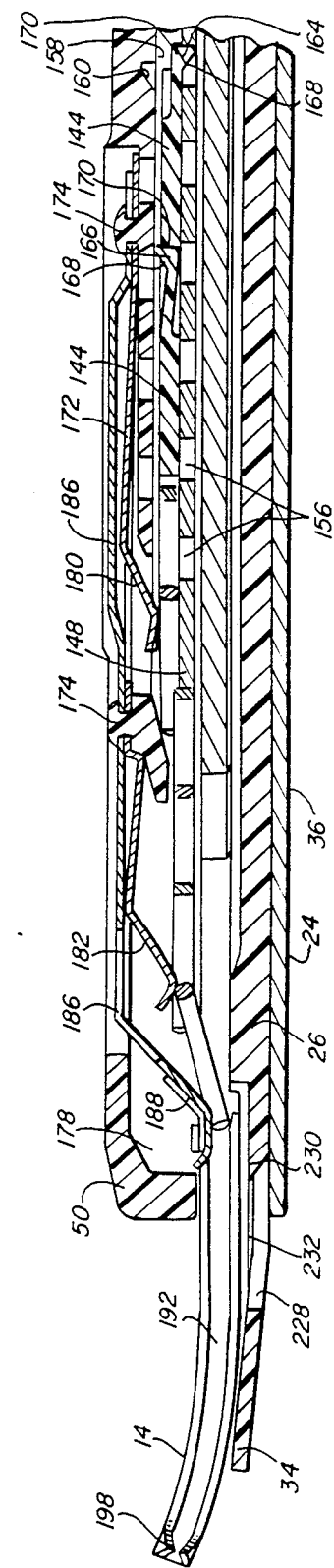
FIG. 8
FIG. 9

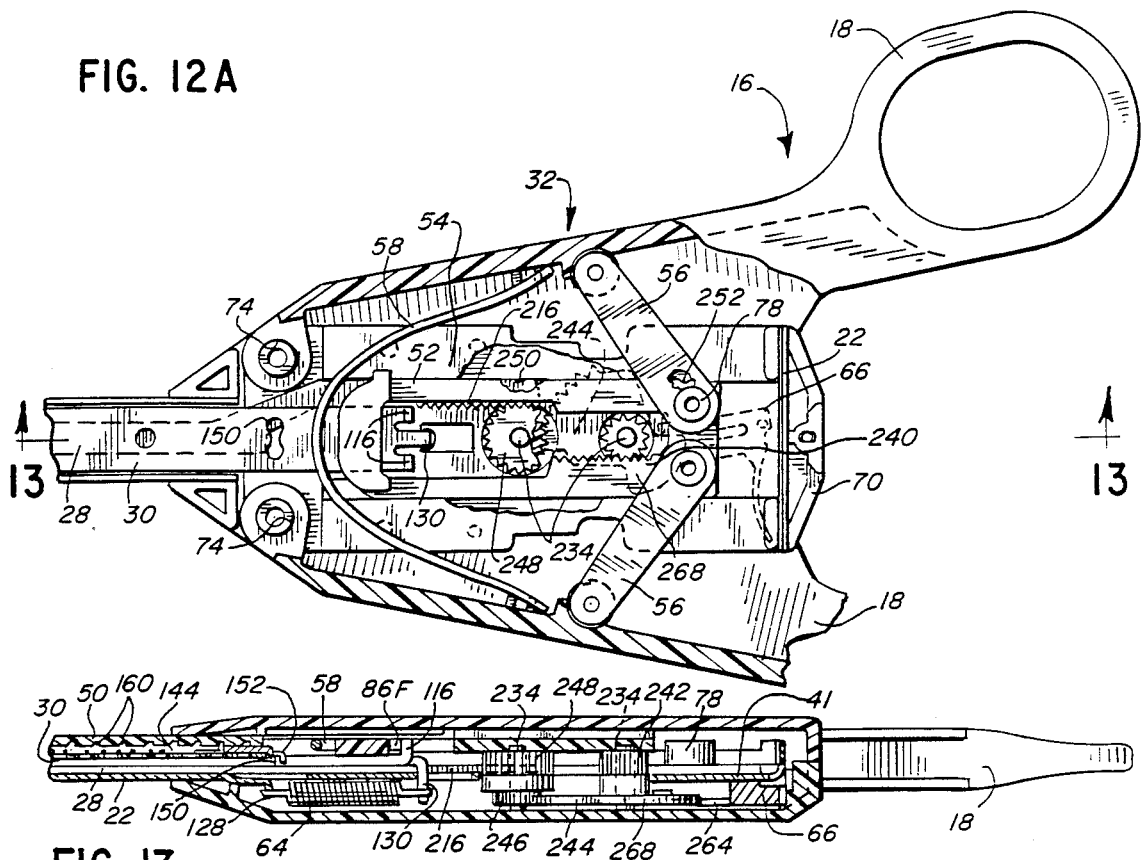
FIG. 12A
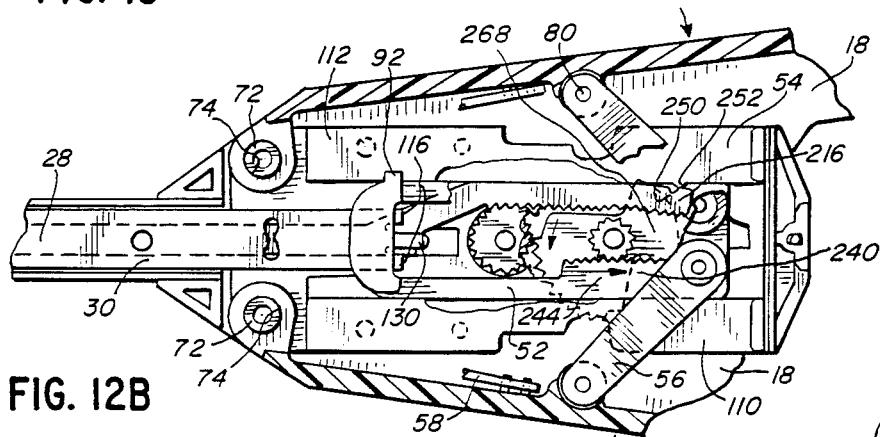
FIG. 13
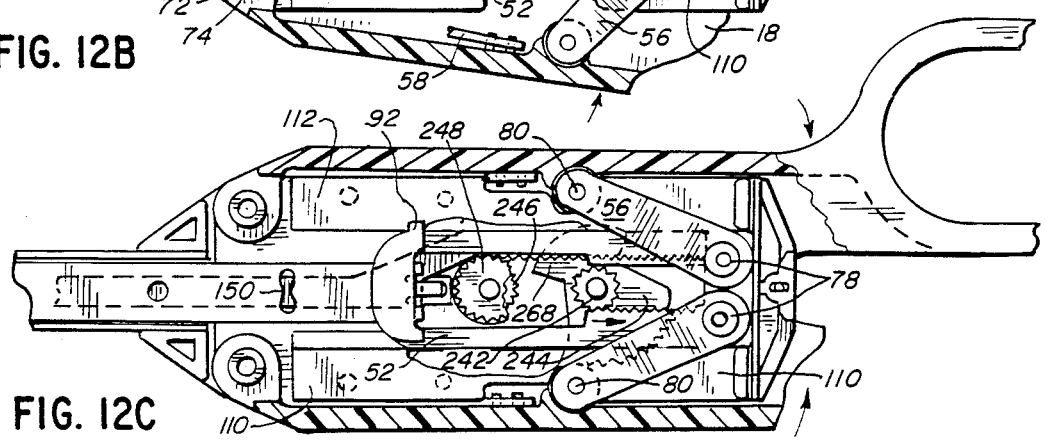
FIG. 12B
FIG. 12C

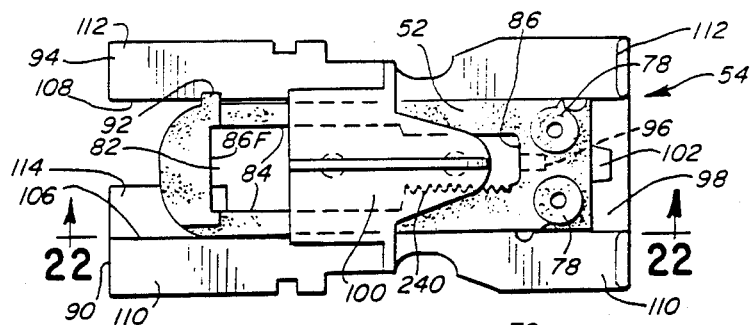
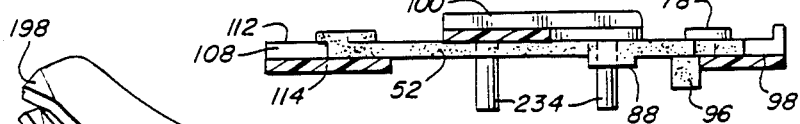
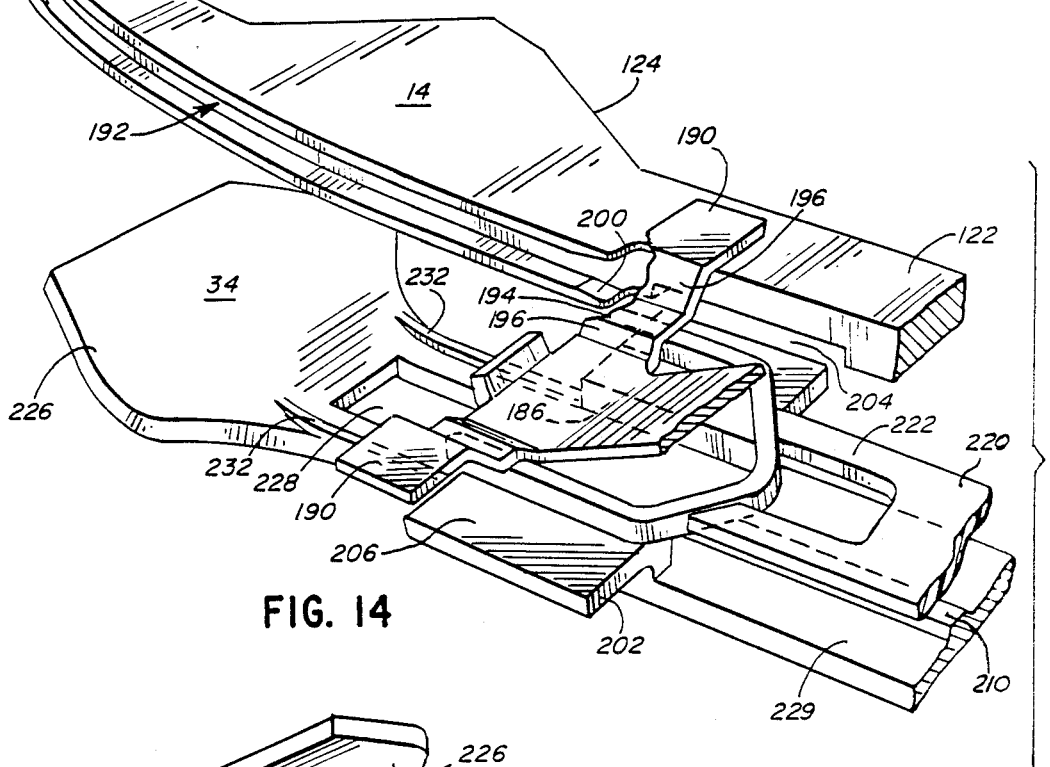
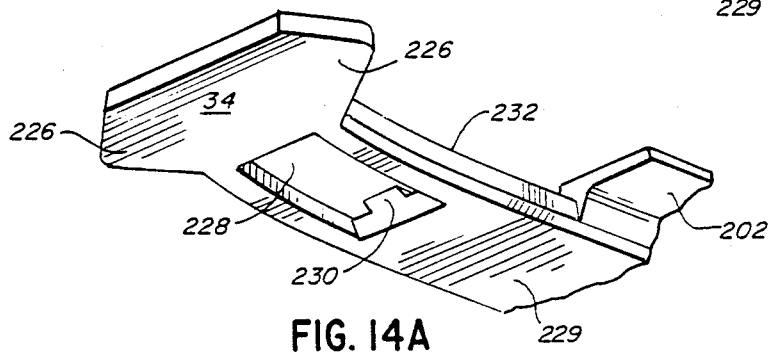

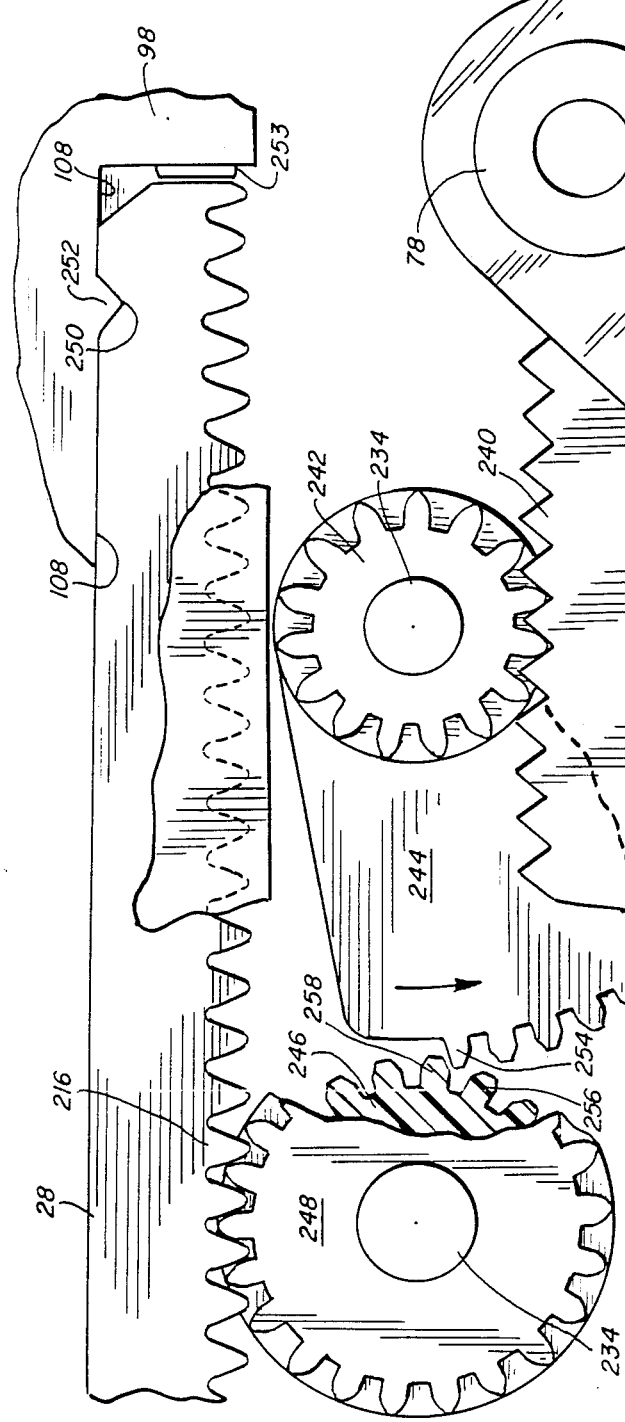
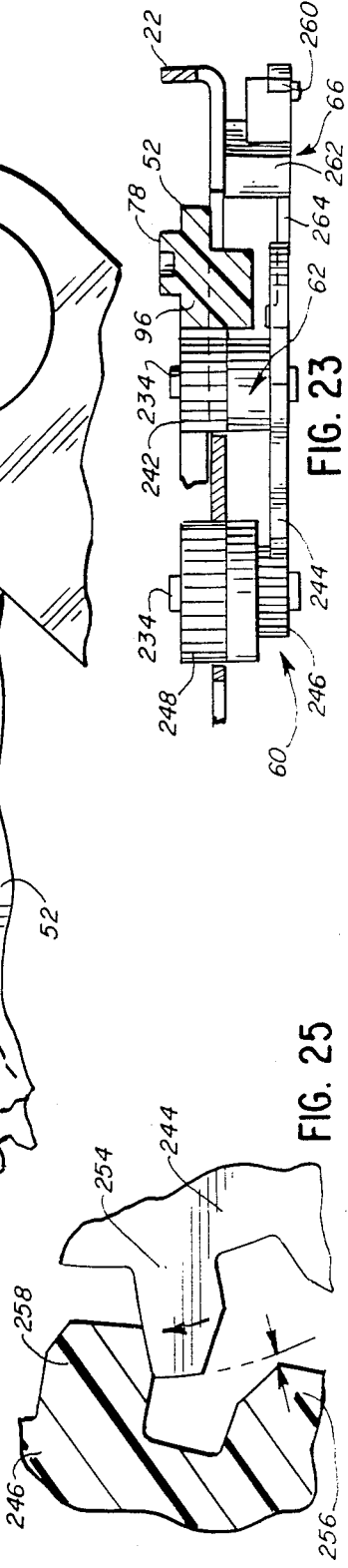
FIG. 24
FIG. 23
FIG. 25

HEMOSTATIC CLIP APPLICATOR FOR APPLYING MULTIPLE HEMOSTATIC CLIPS

BACKGROUND OF THE INVENTION

1. Field Of The Invention

The present invention relates to an improved surgical clip applicator for applying multiple surgical clips to body tissue or blood vessels as necessary during surgical procedures. The clip applicator stores multiple clips, avoiding reloading after application of a clip, and automatically advances the clips to the instrument jaws after placement of each successive clip. Surgical clips are applied to blood vessels, veins, arteries or tissue prior to being severed or cut as required during surgery. In this manner, the loss of blood through the severed vessel is prevented and the flow of blood into the area where the surgeon is operating is also prevented.

2. Description Of The Prior Art

Many methods of constricting blood vessels and the like have been employed over the years. These include pliers or scissors type instruments which are themselves clamped about a vessel as well as the use of small clamps applied to a vessel by a clamp applying instrument. These clamps have ranged widely in shape and size as well as in the manner in which they attach to and constrict a blood vessel.

Generally, there are two types of instruments for applying separate, individual clamping elements or clips to a blood vessel. The first type can be generally referred to as a scissors type because it consists of two arms having jaws at one end and handles at the opposite end with the arms pivotally connected near the jaw end. The instrument is activated similar to a pair of scissors; moving the handles together causes the jaws to clinch and separating the handles causes the jaws to open.

Two variations of the scissors type clip applicator exist. These are either single count clip applicators or multiple count clip applicators. As the names imply, the single clip version only holds one clip at a time and must be continually reloaded after every use. The multiple clip version either integrally contains or is adapted to receive a clip cartridge. The clip cartridge houses multiple clips which are fed to the jaws of the instrument by varying methods.

The second type of clip applicator applies camming principles rather than pivoting to clinch the jaws and deform a clip. Camming is achieved by either reciprocating the jaws within an exterior sleeve or reciprocating the sleeve about stationary jaws. In particular, the jaws can move rearward into the sleeve or the sleeve can move forward past the jaws to accomplish closing of the jaws and clinching of the clip. In either case, a camming action between the outside surface of the jaws and the forward edge of the sleeve close the jaws. This second type of clip application is manufactured in both single count or "one shot" versions or in multiple count versions. Moreover, given the present state of medical technology, these instruments are constructed primarily from plastic in order to produce a low cost instrument which justifies disposal after the single use. Of course, conventional clip appliers as well as the present invention could easily be manufactured from all metal componentry in order to be capable of sterilization and, therefore, reuse. The instrument of the present invention has reciprocating jaws within a stationary sleeve and houses multiple clips. The preferred embodiment is intended to be disposable.

The present invention improves upon the overall componentry and design of reciprocating jaw type clip applicators in general. Specifically, the present invention is constructed around a unitary, one-piece chassis which runs the length of the instrument. This insures that the components attached thereto are always properly aligned and further provides structural strength to the device not found in existing devices constructed from multiple base pieces.

A structural characteristic of reciprocating jaw type instruments which cam the jaws closed is the inability to store clips on the same plane or level as the jaw members. Typically, the jaw members are tuning fork shaped and, therefore, only a limited number of clips can be stored in the space between the jaw arms and subsequently fed to the jaws. Consequently, the clips must be housed in some type of magazine or cartridge either above or below the plane of the jaw arms in order for the instrument to house a sufficient number of clips. To resolve this problem so that clips can be fed to the jaws, the jaws themselves may be made taller or may be increased in height so that there is a deforming portion of the jaws on the same level as the clips to insure proper feed. However, with this structure the jaws of the instrument are at least twice the height necessary, and, therefore, precludes placement of the instrument in small or delicate areas.

The present invention avoids the problem of having to increase the height or size of the jaws by feeding the clips to a position between the jaw arms on the same plane as the jaws and then advancing the clips into the jaws by way of a channel or clip track formed in the jaws. As a result, the jaws are formed at a minimum height to allow placement of the instrument in close, or tight positions.

Indeed, the overall clip housing and clip advancement of the present invention is an improvement over existing designs. Many types and variations of clip housings, cartridges or magazines exist in conventional clip applicators to store and serially advance the clips. However, variations in the manufacture of the individual clips can adversely impair the operation of the instrument. For example, in a clip housing where the clips are abuttingly arranged in a single, forward facing row with the legs of each clip contacting the rearward end or crown of each preceding clip, variations in clip size or non-uniform manufacturing can cause the clips to become unaligned within the housing resulting in a misfire, jam or malfunction of the instrument.

Due to varied clip manufacturing techniques or even variations in quality control, the clip length of any clip can vary compared to any other clip. Clip length is measured from the apex of the clip to the tip of the legs. While the variance in individual clips may be minor, when the clips are arranged in a single, forward facing row, the variations can create significant differences in the overall length of the row. Consequently, because the present instrument is designed to advance the row of clips the length of one clip for each actuation of the instrument, a row of clips which is of improper length can create a jam or a misfeed.

For instance, due to even slight variation in clip length, it is conceivable that a full complement of 35 or 40 clips may be too short or too long in overall length. As a result, despite the design of an instrument to advance the row of clips one clip length for each actuation of the instrument, the forwardmost clip may not be advanced fully into the jaws of the instrument causing a misfeed or the forwardmost clip could be overfed causing the instrument to jam.

To overcome this problem, some conventional clip applicators employ clip housings where the clips are separately stored between a row of teeth and the individual clips are never in contact. In such an arrangement, varied or uneven clip manufacture is of little importance because the clips will be advanced to the next forward incremental position regardless of any discrepancies in clip length. However, the complex structure required for this type of clip advance mechanism is costly to manufacture and it reduces the number of clips which could otherwise be stored in the instrument.

The present instrument overcomes this problem by employing a clip housing or having a dual level row of clips. While the majority of clips are placed in a single, forward facing row upper level, the forwardmost three or four clips are maintained on a lower level. With each actuation of the instrument, the forwardmost clip on the lower level is advanced to the jaws and is replaced on the lower level by the forwardmost clip on the upper level. The lower level of three or four clips effectively minimizes if not negates variations in clip length.

The present invention incorporates still further improvements over conventional clip applicators with respect to its internal design. An improved clip load spring is employed for positively advancing, positioning and stabilizing the forwardmost clip as it is advanced to the jaws. Coupled with the design of the clip housing. The clips are positively controlled at every point within the instrument. As the forwardmost clip on the lower level of the clip housing is to the jaws of the instrument, the spring engages the clip at three points; the apex or crown and the tip of both legs. The clip is moved to a clip load platform which functions to align the clip with clip tracks in each jaw so that the clip can then be advanced into the jaws. This engagement insures an aligned advancement of the clip to a resilient clip load platform disposed between the jaw arms and aligned with clip tracks formed in the jaws. The design of the clip load spring also stabilizes and centerably positions the clip against the platform in order for a clip advancer or ram to engage the clip and push it into the instrument jaws and further allows it to be cammed out from between the jaws during jaw closure thereby avoiding a jamming of the instrument by the spring. As a result of the positive advance, the clip will not become misaligned nor will it jam the instrument during its movement from the lower level of the clip housing to the jaws. Moreover, and of significance, the clip spring allows the instrument to function in any position or at any angle. Because the clip is always positively controlled and advanced, the instrument can operate upside down or in any other position thereby increasing its versatility and value to surgeons.

A further improvement found in the present invention overcomes jamming problems inherent in conventional multiple clip appliers caused by prematurely actuating the instrument while a clip is being transferred to the jaws. Typically this would occur when, after deforming a clip about a vessel, the surgeon does not fully release the handles before a reactuation. In that circumstance, the complete clip feed process may not have occurred, leaving the clip positioned somewhere between the clip housing and the jaws. Consequently, premature reactuation of the instrument may cause the clip to be deformed only partially about a vessel or perhaps internal to the instrument, depending upon the location of the clip. The present instrument employs a lock-out mechanism requiring completion of the clip feed process before the instrument can be reactuated.

The instrument also employs an improved internal drive or transmission mechanism for advancing the clips to the jaws. Particularly, the transmission mechanism includes a gear drive for sequentially actuating the clip feed and clip deformation componentry. The gear drive includes a spur or segment gear having a modified lead tooth profile that allows the transmission mechanism to operate more efficiently and with less force applied by the surgeon.

Not only is the operation and the internal mechanisms of a clip applicator critical but the overall size and exterior shape must allow the device to fit a wide range of hands and also be lightweight and easily maneuvered. Oftentimes a surgeon desires to forego the intended grasp of an instrument and "choke-up" or move his hand closer to the jaw end in order to obtain greater leverage or a more comfortable grasp of the instrument. Operating the instrument in this manner distributes the operating forces throughout the surgeon's entire hand rather than concentrating the forces in his thumb and first one or two fingers. Consequently, palming the instrument in this manner prevents fatigue and tiring of the surgeon's hand allowing him to more effectively undertake longer surgical procedures.

Most present clip applicators and ligators are not suitable for palming. These instruments are susceptible to pinching the operators hands and, because of the internal operating mechanisms, the instruments require a radial closure of the handles which effectively precludes palming the instrument. The present invention is ergonomically designed to fully close with less than ten degrees movement of the handles and, as a result of the design, is operable in the palm of almost any size hand.

OBJECTS OF THE INVENTION

It is general object of the present invention to provide an improved multiple count clip applicator for use during surgery.

It is still another object of the present invention to provide a multiple count clip applicator with an improved transmission mechanism for coordinating the movement of the component parts of the instrument.

It is another object of the invention to provide an improved clip applicator having a dual level clip housing which negates the effects of any variations in clip sizes.

It is another object of the present invention to provide an improved clip applicator which positively positions the clips during advancement in the instrument allowing the instrument to be operated in any position at any angle.

It is a still further object of the present invention to provide a novel lock-out mechanism to prevent actuation of the clip applier before a clip has been properly positioned in the instrument jaws.

It is another object of the present invention to provide a clip applicator which can be comfortably operated in the palm of most surgeons' hands.

Other objects and advantages of the invention will become apparent upon reading the following detailed description and appended claims and upon reference to the accompanying drawings.

DESCRIPTION OF THE DRAWINGS

FIG. 4 is a partial top cross sectional view of the present invention as depicted in FIG. 5.

FIG. 5 is a side cross-sectional view of the present invention in an at rest position with the jaws fully opened and a clip loaded between the jaws.

FIG. 6 is a partial top view of the present invention as shown in FIG. 7.

FIG. 7 is a side cross-sectional view of the present invention with the jaws in a fully closed position.

FIG. 8 is a partial top view of the instrument shown in FIG. 9.

FIG. 9 is a side cross-sectional view of the present invention returning to an unactuated position with the jaws slightly open and the clips being advanced.

FIG. 12A is a partial top view of the actuating mechanism of the present invention in an at rest position with the handles fully open.

FIG. 12B is a partial top view of the present invention showing the handles partially closed with the ram and drawbar extension moving rearward.

FIG. 12C is a partial top view of the present invention showing the handles fully closed.

FIG. 13 is a side cross sectional view of the actuating or transmission mechanism of the present invention.

FIG. 14 is a partial perspective view of the forward end of the instrument of the present invention showing a clip positioned on the clip load platform ready for advancement into the jaws.

FIG. 14A is a partial bottom perspective view of the clipboard platform and tissue stop.

FIG. 21 is a top view of the gear housing and drawbar extension.

FIG. 22 is a side view of the gear housing and drawbar extension taken along line 22—22 of FIG. 21.

FIG. 24 is a partial top view of the transmission mechanism of the present invention showing the ram locked to the gear housing and the modified tooth of the compound spur gear disengaging the idler gear.

FIG. 25 is an enlarged exploded view of the modified tooth of the compound gear reengaging the idler gear.

SUMMARY OF THE INVENTION

The present invention relates to a multiple count clip applier for applying surgical clips to blood vessels, veins or arteries to occlude the flow of blood. The clip applier of the present invention employs a novel transmission mechanism for translating the radial or arcuate closure of the instrument handles into linear or reciprocable movement of the jaws. Indeed, by closing the instrument handles, the jaws of the present invention are retracted into a chassis or main body and cammed closed to deform a clip positioned between the jaws. Upon release of the handles the forwardmost clip in the clip housing is advanced and positioned between the jaws. Moreover, the transmission mechanism employs a unique gear arrangement for sequentially activating the instrument componentry.

The instrument further maintains positive control of the clips as they are fed and transferred through the instrument to the jaws. Included in the positive control are a pair of springs which assist in the transfer of the clips from the clip housing to a clip load platform aligned with the jaws. Moreover, because of this positive control, the instrument can be operated at any angle or in any position and the clips will still be properly advanced to the instrument jaws. To prevent the instrument from being actuated during transfer of a clip from the clip housing to the jaws, the present invention further incorporates a novel lockout mechanism which prevents reactuation of the instrument until after the complete clip feeding process has occurred.

DETAILED DESCRIPTION OF THE INVENTION

The relationship and workings of the various elements of the invention will be better understood by the following detailed description. However, the embodiment of the invention described below is by way of example only and applicants do not limit themselves to the embodiment. Furthermore one should understand that the drawings are not to scale and that the embodiments are illustrated by graphic symbols and fragmentary vies. In certain instances, the applicant may have omitted details which are not necessary for an understanding of the present invention such as conventional details of fabrication and assembly.

When the clip applicator of the present invention is in an unactuated position, a clip is loaded in the jaw and the instrument is ready for use. Clip deformation occurs upon closure of the instrument handles and clip feed to the jaws occurs upon opening of the instrument handles. With the clip in place and ready for deformation, the surgeon can instantaneously place the instrument in position and deform the forwardmost clip about a blood vessel without experiencing any delay associated with having to first advance the clip to the jaws. As a result, the instrument is always ready for use.

Figure 29:
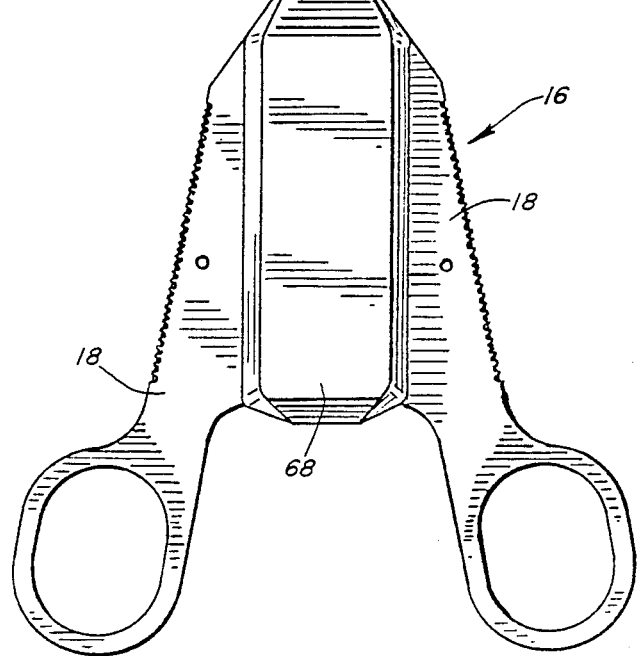
FIG. 29 is a top view of the hemostatic clip applier of the present invention.

Turning now to the drawings, the clip applicator 10 of the present invention, shown in FIG. 29, will be described. As can best be seen, in FIGS. 1 and 12A the clip applicator is provided with a forward operational end 12 which includes a pair of opposed jaws 14 for deforming surgical clips and a rearward actuating end 16 which includes a pair of handles 18. Operatively interconnected between the handles and the jaws is a clip housing or cartridge 20 which stores a supply of surgical clips and feeds a single clip to the jaws of the instrument for each complete actuation of the instrument.

In an unactuated state, a clip is positioned in the jaws ready for deformation about a blood vessel. In operation, the surgeon locates a blood vessel between the clip loaded in the jaws 14 and then completely closes the handles 18 causing the jaws 14 to deform the clip about the blood vessel. Upon opening of the handles 18 the next clip is fed to the jaws 14, and the instrument is ready to be activated again.

Figures 1, 2, 3:
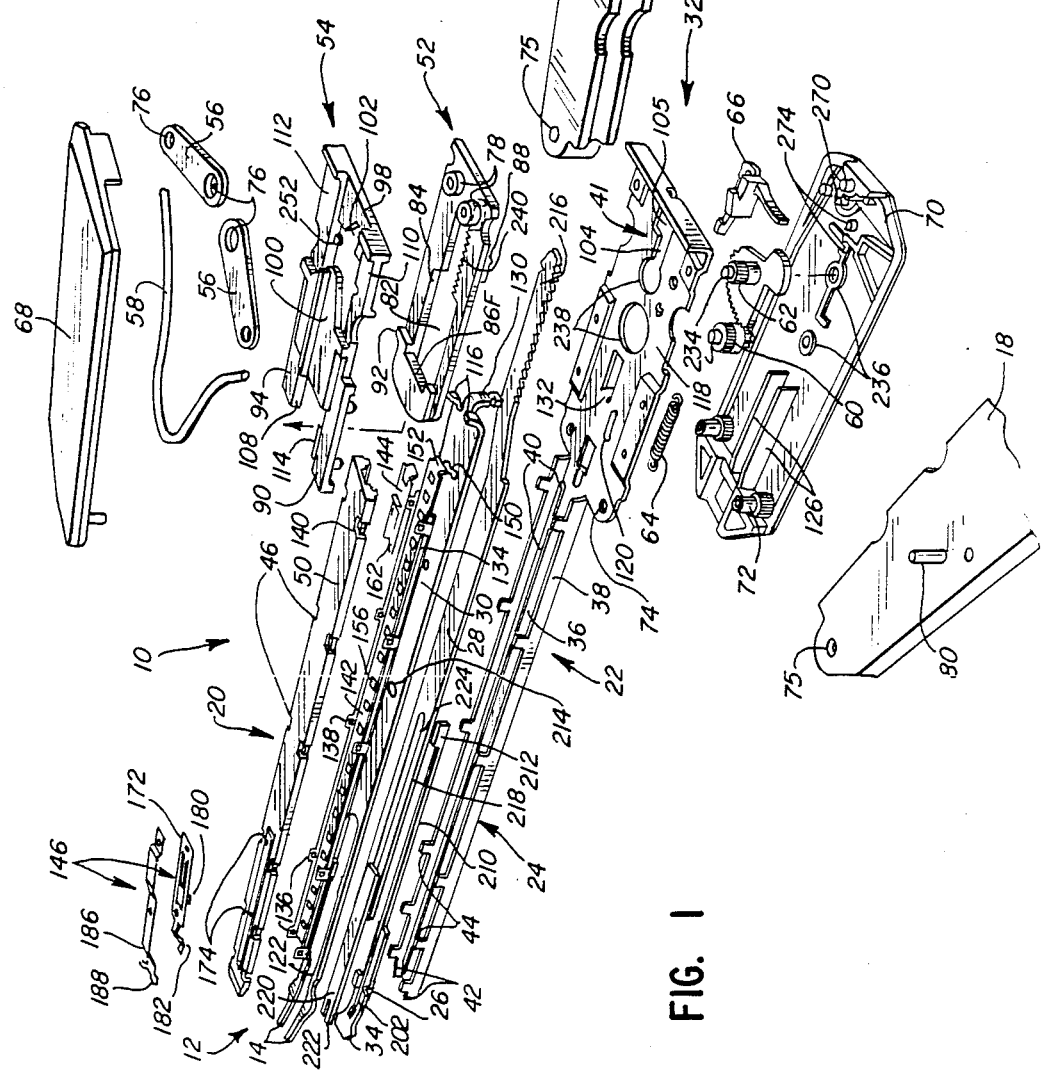
FIG. 1 is an exploded perspective view of the present invention.
FIG. 2 is a cross sectional view of the present invention taken along line 2—2 of FIG. 10.
FIG. 3 is a cross sectional view of the present invention taken along line 3—3 of FIG. 6.

As is best seen in FIG. 1, the preferred embodiment of the applicator is provided with a chassis 22 which acts as the central supporting structure for the entire apparatus. The chassis 22 is a single unitary structure which runs the length of the instrument and provides both structural strength to the instrument and further improves the functioning of the instrument by insuring proper alignment of all other component members. The chassis 22 has an elongated channel shaped forward end 24 which contains and supports the clip housing or clip cartridge 20, a clip load platform member 26 for receiving the clips from the clip housing and for positioning the clips for entry into the jaws 14, a ram or clip advancer 28 for advancing the clips from the clip load platform 26 to the jaws 14 of the instrument, a pair of jaws 14, and a drawbar 30 interconnecting the jaws 14 to the actuating or transmission mechanism 32 of the instrument, (FIG. 12A) and a tissue stop 34 for preventing a blood vessel from pushing a clip back into the instrument once the clip is loaded or positioned in the jaws of the instrument.

Described in more detail, the channel shaped forward end 24 of the chassis 22, shown in FIGS. 2 and 3, includes a base 36 and two sidewalls with a pair of internal shoulders 40 formed at the junction of the base and sidewalls. The forward or distal ends of the two sidewalls 38 are turned slightly inwardly to form a pair of opposed camming surfaces 42. Additionally, the sidewalls 38 are provided with a series of upstanding tabs 44 which engage a series of cooperating slots 46 formed in the clip housing cover 50 to hold the forward end of the instrument together.

The rearward portion 41 of the chassis 22 is an extension of the base 36 of the elongated forward portion 24 and supports the transmission or actuating mechanism 32 of the present invention. The preferred embodiment of the transmission mechanism 32 is shown in FIGS. 1, 12 and 13 and comprises the handles 18, a drawbar extension 52 reciprocably mounted in a gear housing 54 and interconnected to the handles by a pair of links 56, a handle or trigger spring 58, an idler gear 60, a compound gear 62, a drawbar spring 64 and a lockout member 66. As shown in FIG. 1, the applicator is further provided with a cover plate 68 and a base plate 70 for enclosing and protecting these elements. Essentially, the transmission mechanism 32 translates the arcuate closure of the instrument handles 18 into linear movement and sequentially activates both the closing and opening of the jaws 14 and the advancing or feeding of the clips within the instrument.

For a more complete understanding of the instrument, the preferred embodiment will now be described with respect to its functional characteristics.

A. Clip Deformation

As previously stated, when the instrument is in an unactuated state a clip is loaded in the jaws 18 and the handles are completely open (FIGS. 4, 5 and 12A). As seen in FIG. 12B, upon closure of the handles 18, the drawbar extension 52 is caused to move rearwardly within the gear housing 54 as a result of its interconnection to the handles 18 by a pair of links 56. The handles 18 pivot about a pair of pivot pins 72 disposed on the bottom cover and extending through a pair of apertures 74 in the chassis 22. The pins 72 are engaged in a bore 75 formed at the forward end of the handles 18. Similarly, each link 56 is provided with an aperture 76 at each end to rotatable engage the upstanding pivots 78 at the rearward end of the drawbar extension 52 and to rotatably engage a link pin 80 mounted midway in the handle 18.

In the preferred embodiment, the links are attached to the jaw bar extension at separate, symetric locations rather than being overlapped and attached to the drawbar extension by a single pin. This latter, nonsymetric method of attachment creates a torque on the instrument during closure or, the handles which attempts to turn the instrument in the surgeon's hand during use. Because of this design, the force acting on the instrument from opposite directions during closure of the handles balances and the instrument is more stable in the hand of the surgeon.

The drawbar extension 52 is essentially rectangular in shape and is provided with an elongated slot 82 which defines the interior sidewalls 84 and the interior endwalls 86 of the drawbar extension. As shown in FIGS. 21 and 22, the drawbar extension 52 is further provided with a pair of extensions or slide tabs to maintain the position and balance of the drawbar extension as it reciprocates within the gear housing 54. The first tab 88 extends downwardly from the bottom of the drawbar extension and slidably engages one sidewall 90 of the gear housing 54. The second tab 92 extends outwardly from the front end of the drawbar extension and slidably engages the upper surface of the other sidewall 94 of the gear housing (FIGS. 12C, 24). A third larger tab 96 or safety lug extends downwardly from the bottom of the drawbar extension near the interior rear end wall (FIG. 22). This lug 96 cooperates with a lockout member 66 (FIGS. 26–28) to provide the instrument with a safety feature for preventing actuation of the instrument while a clip is being transferred from the clip housing 20 to the jaws 14.

The gear housing 54 is mounted to the rear portion of the chassis 22 by means well known in the art and is comprised of two sidewall portions 90 and 94 interconnected by a base plate 98 and an axle plate 100 (FIGS. 1, 21 and 22). Both the base plate 98 and the rear portion of the chassis are provided with cut out portions 102 and 104, respectively, to allow for the reciprocating movement of the drawbar safety lug 96. Each sidewall portion 90 or 94 is defined by a vertical wall 106 and 108, respectively, and a top surface 110 and 112, respectively, extending outwardly from the vertical wall with the left hand vertical 106 wall further provided with an inwardly extending slide tab 114. In operation, the drawbar extension 52 reciprocates between the vertical walls 106 and 108 of the gear housing 52. The first and second slide tabs 88 and 92 of the drawbar extension 52 and the slide tab 114 and base plate 98 of the gear housing 54 cooperate to maintain and slidably support the drawbar extension 52 during this movement.

A drawbar 30 is disposed in the forward end 24 of the chassis 22 and rests on top of the internal shoulders 40 (FIGS. 1 and 3). During its rearward movement, the forward interior end wall 86F of the drawbar extension engages a pair of upstanding fingers 116 on the rear end of the drawbar thereby causing the drawbar 30 to move rearward in tandem with the drawbar extension 52 (FIG. 12B). In its rearward movement, the rear end of the drawbar maintains its elevated position with respect to the base 14 of the chassis 22 by sliding on an upwardly protruding nipple 120 formed in the base of the chassis (FIG. 1) and also by sliding on top of the ram or clip advancer 28 disposed beneath the drawbar 30 (FIG. 12C).

The jaws 14 of the instrument are interconnected to the forward end of the drawbar 30 by means of a pair of resilient or flexible jaw arms 122 (FIGS. 1 and 14) and upon rearward movement of the drawbar 30 the jaws 14 are also drawn rearward and ultimately cammed closed (FIGS. 4 and 6). The exterior edges of the jaws extend laterally outwardly to form a pair of camming surfaces 124. During the rearward movement of the jaws 18, these camming surfaces 124 contact a pair of inwardly directed vertical shoulders 42 formed at the distal end of the forward portion 24 of the chassis 22 which cause the jaws to be cammed closed thereby deforming the forwardmost clip positioned in the jaws about a blood vessel. At this point (FIGS. 6 and 12C), the handles 18 will be completely closed and rearward movement of the jaws will be terminated.

Upon release of the handles 18 the instrument is caused to return to its unactuated position under the influence of the drawbar spring 64 and the handle spring 58 (FIGS. 1 and 13). The drawbar spring 64, disposed between the upstanding walls 126 formed in the bottom cover 70 of the instrument, is attached at its forward end to a downwardly depending finger 128 formed from the rear portion of the chassis 22 and at its rearward end to a downwardly depending finger 130 located at the rearward end of the drawbar. Both fingers are provided with notched ends to securely engage the spring. The finger 130 of the drawbar reciprocates in a slot 132 formed in the rearward portion of the chassis. The handle spring 58 extends between and interconnects the two handles 18. During closure of the instrument and deformation of a clip, the drawbar spring 64 is subject to tensioning and the handle spring 58 is subject to compression to thereby store energy in the springs. Upon release of the handles these two springs coact to open the handles 18 and to return the drawbar 30 and drawbar extension 52 to their forwardmost positions which thereby causes the jaws 18 to move forward and open as well. As will be discussed below, the forces supplied by these springs also act to advance and feed a clip to the jaws.

B. The Clip Housing

The dual level clip housing or cartridge 20 of the present invention is disposed along the forward elongate portion 24 of the chassis 22 and above the drawbar 30 and jaw arms 122 (FIG. 1). The clip housing 20 is comprised of a skirt 134 which rests on the drawbar 30 and a housing cover 50 which, amounts on top of the skirt to form a clip storage cavity 135. In particular, as seen in FIG. 1, the skirt 134 is provided with a pair of side walls 133 136 extend upwardly from the side walls 133 and have small apertures 138 formed therein which lockably engage multiple outwardly projecting knobs 140 formed in the receptive slots 46 spaced along the clip housing cover 50. In addition, the clip housing further comprises a ratchet advancer 142 which reciprocates within the skirt 134 and is interconnected to the drawbar 30 at its rearward end, a pawl 144 for advancing the clips within the clip housing and a pair of springs 146 disposed at the forward end of the housing cover 50 (FIGS. 5, 7, 9 and 11) for assisting in advancement of the clips to the jaws of the instrument. The ratchet advancer 142 is further provided with a forwardly extending nose or kicker 148.

Besides assisting in closing the jaws 14 of the instrument, the rearward movement of the drawbar 30 also actuates the mechanism for advancing the clips within the clip housing. The drawbar 30 is provided with a horizontal slot or opening 150 near its rearward end which engages a downwardly depending flange 152 affixed to the rearward end of the ratchet advancer 142. The ratchet advancer 142 slides on top of the skirt 134 member and is guided in its movement by a first pair of shoulders 154 formed in the clip housing cover (FIG. 3). The clips are abuttingly arranged in a continuous, forward facing line on top of the ratchet advancer 142 with the final rearwardmost clip engaged in the front portion of pawl 144 (FIG. 9). The housing cover 50 is further provided with a second pair of inwardly directed shoulders 155 for aligning and guiding the clips resting on the ratchet advancer 142 (FIG. 3). The ratchet advancer 142 is provided with a series of recesses or cutout portions 156 for engaging and advancing the pawl 144 (FIG. 1). The clip housing cover 50 is also provided with a ratchet surface 158 formed along the inside upper surface having cut out portions 160 for cooperating with the ratchet advancer 142 to engage and advance the pawl 144 (FIGS. 3 and 9).

As can further be seen in FIG. 1, the pawl 144 is provided with a notched front end 162 adapted to receptively engage the rearward end or crown of the clips. Additionally, as shown in FIG. 9 the pawl 144 is provided with a downwardly extending resilient flange 164 and an upwardly extending resilient flange 166 for engaging the cut out portions or recesses of the ratchet advancer 156 and the ratchet surface 158 of the housing cover 50, respectively. Each resilient flange is provided with a beveled forward surface 168 and a vertical rearward surface 170. The pawl 144 is activated by reciprocating movement of the ratchet advancer 142. The flanges alternately engage and disengage the recesses of the ratchet advancer 142 and the ratchet surface 158 of the housing cover 50 to advance the clips in conjunction with the reciprocating motion of the ratchet advancer 142.

As stated previously, the clip cartridge has two levels of clips. Besides being stored on the ratchet advancer 142, the preferred embodiment of the present invention places three or four clips on the skirt 134 in front of the ratchet advancer 142. The clip snap spring 172 is mounted on a pair of posts 174 on the clip housing cover 50 (FIG. 9) and assists in the transfer of clips from the ratchet advancer 142 to the skirt 134 or lower level. As shown in FIGS. 4 and 5, the skirt 134 terminates before reaching the internal forward wall 176 of the clip cover to thereby define a breach 178. The breach 178 provides the passage for the clips to be transferred from the skirt or lower level 134 or to the jaws 14 of the instrument. By employing this multiple level clip feed arrangement, the forward end of the instrument can be provided with a small profile allowing the instrument to be operated in small areas.

As seen in FIGS. 4 and 5, the instrument is in an unactuated position with the forwardmost three clips on the skirt 134 and the fourth clip in transition from the ratchet advancer or upper level 142 to a position on the skirt or lower level 134.

In operation, FIGS. 1, 12, and 13, as the drawbar 30 moves rearwardly the engagement of the downwardly depending flange 152 of the ratchet advance 142 with the cut out portion 150 of the drawbar 30 causes the ratchet advancer 142 to move rearwardly. Similarly, the clips resting on the ratchet advancer 142 are caused to be drawn rearwardly. However, rearward movement of the clips is prevented because the pawl 144 is prevented from moving rearwardly due to engagement of the vertical rearward edge 170 of the upwardly extending resilient flange 166 in the applicable recess of the ratchet surface 158 in housing cover 50. At the same time, the downwardly depending resilient flange 164 is caused to be cammed upwardly as the ratchet advancer 142 travels rearwardly due to the engagement of the beveled forward surface 168 of the downwardly depending resilient flange 164 with the forward edge of the applicable recess in the ratchet advancer 142. As a result, while the clips have not physically moved relative to the instrument, the clips have all moved forward on the ratchet advancer as a result of its rearward movement.

During this same rearward travel of the ratchet advancer 142, the forwardmost clip on the ratchet advancer is transferred from the ratchet advancer, FIGS. 4 and 5, to the upper surface of the skirt 134, FIGS. 6 and 7. As can be seen in FIG. 5, before the ratchet advancer 142 begins its rearward movement, the forwardmost clip on the ratchet advancer is already in transition to the skirt or lower level 134. This clip is positively held in transition between the rear tine 180 of the clip snap spring 172 and the kicker 148 extending from the front end of the ratchet advancer 142. As the ratchet advancer 142 retracts the kicker 148 ultimately is removed from beneath the clip and the clip snap spring 172 positions the clip on the skirt 134 while maintaining engagement with the crown or apex of the clip. (FIG. 7).

When the ratchet advancer 142 completes its rearward travel, the jaws are completely clinched and the kicker 148 is positioned immediately behind the last or rearwardmost clip on the skirt 134 (FIGS. 6 and 7). At this same point in the sequence of the instrument, the forwardmost clip on the skirt 134 is positively secured in position against the skirt by means of the front tine 182 of the clip snap spring 172 and prevents the clip from falling off the skirt and into the breach 178 of the jaws. In the preferred embodiment, four clips are position on the skirt at this point. It is certainly contemplated that fewer or more clips could be placed on this lower level, however, as the number of clips increases the effects of variations in clip length become more pronounced. The other clips are held in place by the shoulders 154 formed in the clip housing cover (FIG. 3). This allows the surgeon to maneuver and operate the instrument in various positions without risk of the clips moving or coming out of position and potentially jamming or fouling the instrument.

As the handles 18 are released, the drawbar extension 52 is caused to move forward under the influence of the drawbar spring 64 which, in turn, causes the ratchet advancer 142 to move forward as a result of their interconnection. Forward movement of the ratchet advancer 142 also drives the pawl 144 forward as the backwall of the appropriate ratchet advancer recess engages the vertical wall 170 of the downwardly depending flange 164 of the pawl 144. The forward movement of the pawl 144 relative to the stationary clip housing cover 50 causes the forward beveled surface 168 of the upwardly extending flange 166 of the pawl 144 to engage the applicable recess in the ratchet surface 158 of the clip housing cover 50 and be cammed downwardly thereby allowing the pawl 144 to move freely forward. The pawl 144 and recesses 156 and 160, respectively, formed in the ratchet advancer 142 and ratchet surface 158 of the clip housing cover 50 are designed in order that the pawl 144 advance one recess for each single actuation of the instrument. The resulting effect is that the clips on the ratchet advancer move forward one clip length as well.

Forward movement of the ratchet advancer 142 also causes the kicker 148 on the forward end of the ratchet advancer 142 to engage the crown or apex of the fourth clip on the skirt 134 and advance the four clips (FIGS. 8 and 9). As the forwardmost clip is pushed forward, the legs of the clip extend past the end of the skirt 134 and into the breach 178 above the clip load platform 26 and the crown or apex of the forwardmost clip causes the forward tine 180 of the clip snap spring 172 to deflect upwardly (FIG. 7).

Further forward movement causes the legs of the clip to contact the clip load spring 186 thereby forcing the clip downwardly toward the clip load platform 26 (FIGS. 8 and 9). The clip load spring 186 in part overlies the clip snap spring 172 and is mounted to the clip cover 50 on the same pair of posts 174 as the clip snap spring 172 (FIG. 9). As best seen in FIGS. 2 and 14, the tine 188 of the clip load spring 186 is provided with a pair of stepped laterally extending members interconnected by a pair of outwardly slanted segments. The uppermost laterally extending surfaces 190 abut the top of the jaw 122 arms and prevent the clip load spring 186 from overpowering the clip load platform 26 and forcing the clip below the clip tracks 192 formed in the jaws channels. These uppermost outwardly extending lateral surfaces also act as safety features to prevent the clip load spring from becoming trapped between the jaw arms 122 to prevent closure of the jaws.

The intermediate laterally extending surfaces 194 and the first pair of outwardly slanted surfaces 196 create a first recess for engaging the legs of a clip. As seen in FIGS. 2 and 14, this first recess horizontally centers the clip on the clip load platform 26. Moreover, as the jaw arms 122 close the outwardly slanted segments 196 cause the clip load spring 182 to be cammed upwardly out of the way of the closing jaws arm 122.

Figure 10:
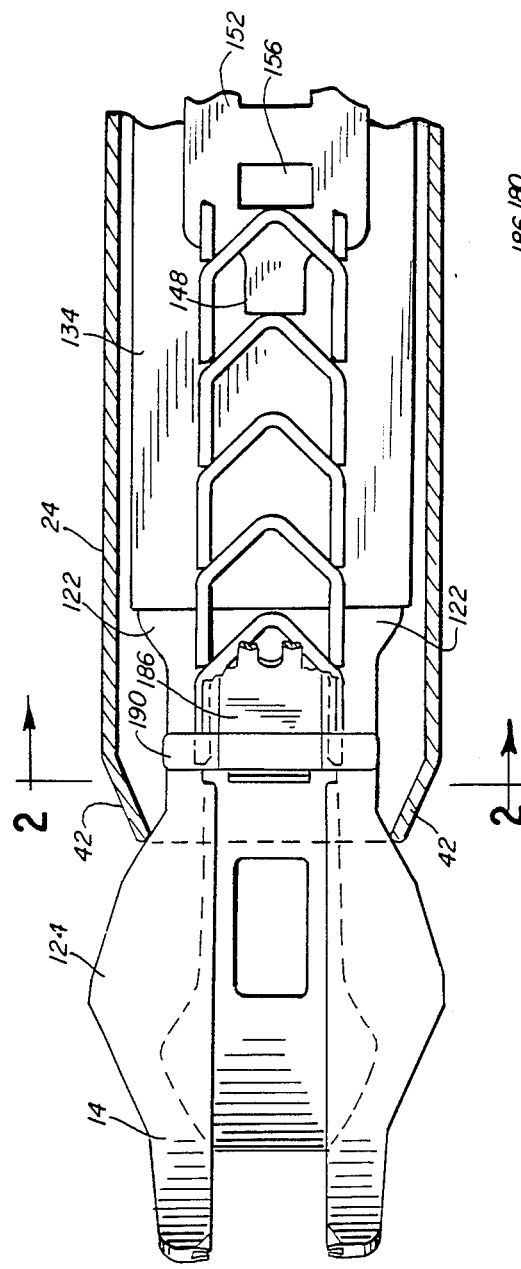
FIG. 10 is a partial top view of the instrument shown in FIG. 11.
Figure 11:
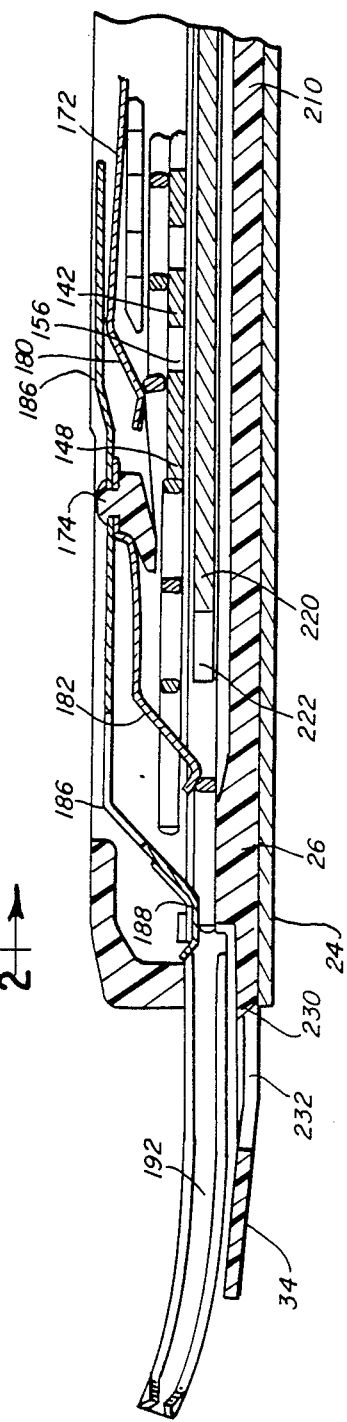
FIG. 11 is a side cross-sectional view of the present invention returning to the at rest position with the jaws fully open and the forwardmost clip on the clip load platform.

More specifically, the forwardmost clip is engaged at three points, FIG. 9, and as it is advanced over the edge of the skirt 134, the legs of the clip are first driven downwardly by the clip load spring 186 and subsequently, after the clip has been pushed off the skirt 134 and fully into the breach 178, the crown apex of the clip is driven downwardly by the front tine 180 of the clip snap spring 172 until the clip is positioned on the clip load platform 26 (FIGS. 10 and 11). The positive coaction of the clip load spring 186 and clip snap spring 172 in driving the clip to the clip load platform 26 allows the instrument to be operated in any position without fear of the clip being misfed due to gravity or other negative factors. Moreover, the opposing actions of the clip load spring 186 and the resilient clip load platform 26 act to position or align the clip with the clip tracks 192 formed in the jaws 14 (FIG. 14) for subsequent advancement of the clip to the jaws.

C. Positioning The Clip In The Jaws

As can be seen in FIG. 14, the jaws 14 of the instrument are provided with a track or channel 192 for guiding the clip between the jaws and for positioning and holding the clip during the deformation. In addition, the tips 198 of the jaws are crimped in order to prevent the clip from falling out of the front of the instrument and potentially being lost within the wound of a patient or simply delaying surgery by having to reactuate the instrument in order to advance another clip to the jaws. As also can be seen, the clip tracks are provided with sloped entry surfaces 200 to further facilitate reception and advancement of the clip. It is important that a clip be properly positioned or aligned prior to entry into the tracks 192 in order to avoid the clip becoming jammed or misfed as it slides to the forward part of the jaws. Consequently, the clip load platform 26 is resiliently affixed to the chassis of the instrument with an upward bias in order that it provide an upwardly directed spring action to counterbalance the downward action of the clip load spring 186 and clip snap spring 172. Both the clip load platform 26 and clip load spring 186 are designed to center the clip both vertically and horizontally for proper alignment with the clip tracks 192.

As can best be seen in FIGS. 1 and 2, the clip load platform 26 is mounted on the bottom of the forward portion of the chassis 22 between the two shoulders 40 and is biased upwardly toward the jaw arms. The clip load platform 26 is further provided with a pair of outwardly extending platform members or ears 202 which abut and nest within a pair of cut outs 204 in the jaw arms (FIGS. 2 and 14). As a result, the upper surface 206 of the clip load platform 26 is coplanar with or slightly above the lower surface of the clip tracks and the clip is always properly positioned for advancement into the jaws. Because the jaw arms 122 retract during operation of the instrument, the clip load platform 26 must be designed to move in tandem with the jaw arms. To that end the clip load platform 26 has a rearwardly extending arm or center rib 210 which terminates in an upstanding guidepost 212. The guidepost extends into and engages a slot 214 formed in the drawbar 30 which allows the clip load platform to retract as the drawbar 30 retracts.

The clip is moved from the clip load platform 26 to the jaws 14 of the instrument by means of a reciprocating ram or clip advancer 28. The ram 28 is an elongated member with a gear rack 216 disposed at its rearward end and a pair of spaced extension arms 218 at its front end (FIG. 1). As is best shown in FIG. 1, a clip engaging member 220 is mounted on top of the extension arms 218 and extends forward therefrom and terminates in a notched front end 222 for engaging the apex or crown of a clip. The ram reciprocates along the base 36 of the forward end 24 of the chassis 22 between the opposed shoulders 40 as shown in FIG. 3. The slot 224 formed between the extension arms 218 allows the ram to reciprocate without interfering with the engagement of the clip stop platform guidepost 212 with the drawbar 30.

As shown in FIGS. 4 and 5, the instrument is in the fully open position and the ram 28 is abutting the apex or crown of the clip. When the instrument is unactuated, the ram 28 functions as the clip stop to prevent the clip from being forced back into the instrument. Such an occurrence could happen merely by gravity or when a surgeon moves the instrument forward after placing the clip about a blood vessel. This forward movement of the instrument in conjunction with the stationary position of the blood vessel causes the blood vessel to force the clip back into the instrument potentially causing a jam and certainly causing delay and frustration in the surgical procedure while the errant clip is retrieved.

However, in the present invention the ram 28 cannot remain in its forward position during actuation of the instrument. The presence of the ram would prevent the jaws 18 from completely closing and this would prevent the clip from being completely clenched about the blood vessel. Consequently, the instrument provides for the ram to be withdrawn rearwardly into the instrument before the jaws are closed. Because removal of the ram leaves the clip without a clip stop, a tissue or vessel stop 34 is incorporated at the distal end of the clip load platform 26 to function in place of the ram 28 during closure of the jaws in the absence of the ram 28 to prevent a tissue or blood vessel from pushing a clip into the instrument.

As best shown in FIGS. 14 and 14A, the tissue stop 34 is positioned beneath the jaws 14 of the instrument and has two lateral extensions 226 which allow the tissue stop 34 to span the open jaws 14 and prevent the tissue stop from being caught between the instrument jaws.

While it is intended that every clip will be properly formed about a blood vessel, it is realized that the present invention will be operated or tested prior to use in surgery or simply by potential purchasers in an environment without vessels or tissue for the clips to be clamped around. As a result, the deformed clips will be unattached to any stationary object and, therefore, free to possibly fall or slide into the instrument and cause a jam. To remove this remote possibility, the tissue or vessel stop is further provided with a rectangular 228 hole 228 in the base 229 and a raised, forwardly slanting tooth 230 at the back side of this hole (FIG. 14A). The tooth 230 is an extension of the extension arm or center rib 210 of the clip load platform 26. In addition, the side edges of the clip load platform are raised to create shoulders or side walls 232 on the clip load platform base 229. Consequently, if the instrument was actuated without a vessel or tissue, the deformed clip will slide down the base 229 of the clip load platform 26 guided by the outside shoulders 232 and would fall harmlessly through the hole 228 either before or after striking the raised tooth 230 at the back end of the hole. The forward slant of the tooth 230 acts to direct the clip downward.

Reciprocal movement of the ram 28 is controlled by movement of the drawbar extension 52 through the interconnection of the ram 28 to the drawbar extension 52 by a compound gear 62 and an idler gear 60. As shown in FIGS. 1, 13 and 25, the compound gear 62 and the idler gear 60 are mounted on separate axles 234 formed in the axle plate 100 of the gear housing 54 and which rest in a pair of seats 236 formed on the inside surface of the bottom cover 70 of the instrument. A pair of apertures 238, aligned with the axles 234, are formed in the center of the chassis 22 to allow the compound gear 62 and idler gear 60 to extend through the chassis 22. As the drawbar extension 52 moves rearwardly, a gear rack 240 formed on the inside surface of the drawbar extension 52 causes the upper pinion gear 242 of the compound gear 62 to rotate counterclockwise. As a result, the gear segment 244 of the compound gear 62, disposed below the chassis 22, is caused to rotate counterclockwise and engage the lower pinion gear 246 of the idler gear 60. Rotation of the lower pinion gear 246 of the idler gear 60 causes simultaneous rotation of the upper pinion gear 248 of the idler gear 60 which, in turn, engages the gear rack 216 of the ram 28 disposed at the rearward end of the ram. As a result, rearward movement of the drawbar extension 52 causes the ram 28 to withdraw into the instrument between the idler gear and left hand vertical wall 108 of the gear housing 54 (FIGS. 12B and 24). At a specific point, the gear segment 244 will disengage the lower portion 246 of the idler gear 60 causing the idler gear 60 to stop rotating. At this point, the ram 28 has withdrawn sufficiently from between the jaws 14 to allow the jaws to be cammed closed without interference from the forward end of the ram 28.

It is critical that the idler gear 60 maintain this position in order that it be properly positioned to be reengaged by the gear segment 244 on the return stroke of the instrument. Consequently, at this same point in time, a notch 250 in the rearward end of the ram 28 is caused to engage a protruding tab 252 on the sidewall 108 of the gear housing 54 to lock the ram 28 and the idler gear 60 in place during further actuation of the instrument (FIG. 24). The preferred embodiment may include a pad 253 disposed on the base plate 98 of the gear housing 54 to help position the ram when it is locked in place (FIG. 24). As best seen in FIG. 12B, the ram 28 is flexible so that it can pass over the tab 252 before locking in place. If the ram 28 did not lock the idler gear 60 in place, the idler gear 60 may rotate after the gear segment 244 is disengaged. As a result, when the gear segment 244 attempts to re-engage the idler gear 60 the gear teeth will not be synchronized and a jam could occur. As an alternative embodiment it is contemplated that a separate member, other than the ram 28 could be used to lock the idler gear 60 in position.

Because the compound gear 62 rotates as a result of the linear movement of the drawbar extension 52, the range of rotation of the compound gear 62 is limited by the space available for linear movement of the drawbar extension 52. With the movement of the drawbar extension 52 and compound gear 62 limited, it is desirable to minimize the amount of rotation of the compound gear 62 necessary to safely withdraw the ram 28 from the jaws 14 and allow closure of the jaws. In the preferred embodiment of the present invention, a step up ratio of 6:1 between the gear segment and upper pinion gear of the compound gear is sufficient to achieve the necessary rotation of the compound gear given the limited linear movement of the drawbar extension. Other ratios could be equally satisfactory upon modification of the gears.

Upon release of the handles 18, the handle spring 58 forces the handles 18 to open and the drawbar spring 64 acts to pull the drawbar 30 forward. These two forces, in turn, cause the drawbar extension 62 to move forward which causes the compound gear to reverse rotation and ultimate reengage the idler gear 60. The counter rotation of the idler gear 60, forces the ram 28 forward, disengaging it from its locked position, wherein it engages a clip which has been disposed on the clip load platform 26 by means of the clip load spring 186. As the ram 28 moves forward, it engages the clip resting on a clip load platform 28 and advances the clip through the clip tracks 192 formed on the jaws 14 to a forward position in the jaws.

Upon inspection of FIGS. 24 and 25, it will be noted that the lead or re-engaging tooth 254 of the gear segment of the compound gear 62 has a modified profile. The modified profile serves two functions; to re-engage the idler gear without jamming and to overcome the static forces acting on the idler gear from its engagement with the locked ram. The shaved or cut back profile of the re-engaging tooth on the gear segment 244 coupled with the idler gear 60 being locked in position guarantee that the re-engaging tooth 254 will miss tooth 256 and engage tooth 258 on the idler gear 60. Moreover, to overcome the static forces holding the idler gear in position, the re-engaging gear 244 must apply a force larger than the restraining force acting on the idler gear 60. Normally, when the lead tooth of a re-engaging gear along the interface between the two gears in contact is not modified, but has the same rounded profile as the other teeth, the force applied by the re-engaging gear is not fully directed to overcoming the static forces at work; only a component of this force is actually applied to overcome the static forces. In the preferred embodiment, as seen in FIG. 25, the result of the modification is that the total force applied by the re-engaging gear is normal or substantially normal to the plane where the teeth engage thereby applying the total force or a substantial portion of the total force applied by the gear segment to initiate movement of the idler gear. Consequently, the design is more efficient and requires less force to put the idler gear in motion.

D. The Lock-out Mechanism

Figure 26:
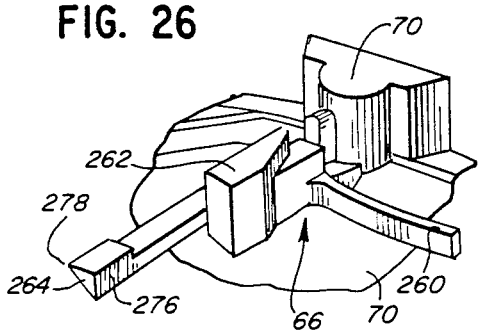
FIGS. 26 and 27 are elevated perspective views of the lockout member of the present invention.
Figure 27:
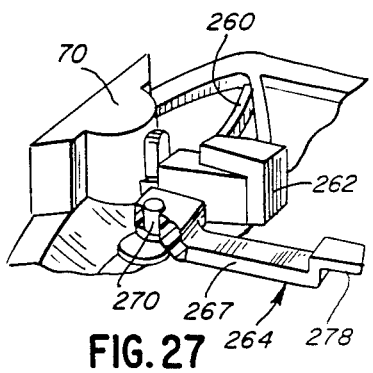
Figure 28:
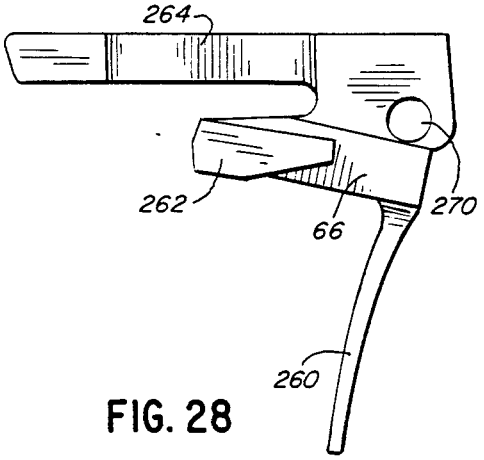
FIG. 28 is a top view of the lockout member of the present invention.

The present invention is also provided with a safety or lock-out mechanism which prevents actuation of the instrument while a clip is being advanced from the clip housing to the jaws. The lockout member is shown in FIGS. 26-28. As can be seen, the lockout member 66 has an elongate spring arm 260, a center lockout lug 262 and an elongate camming arm 264. The lockout member 66 is activated by a cam 268 disposed opposite the gear segment 244 on the compound gear 62 and rotates about a pivot 270 disposed on the bottom cover 70 of the instrument (FIG. 1). The entire lockout mechanism is shown in a side view in FIG. 23.

Figure 15:
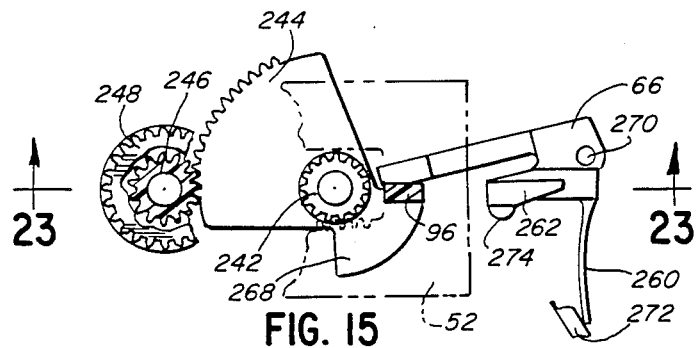
FIG. 15 is a top view of the lockout mechanism of the present invention shown while the instrument is in an unactuated position.
Figure 16:
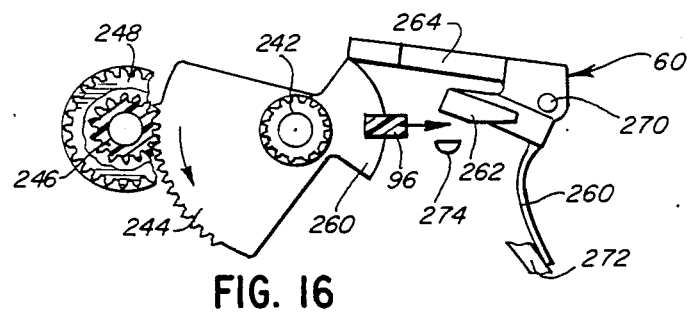
FIG. 16 is a top view of the lockout mechanism of the present invention shown partially actuated when the drawbar extension has just engaged the drawbar.
Figure 17:
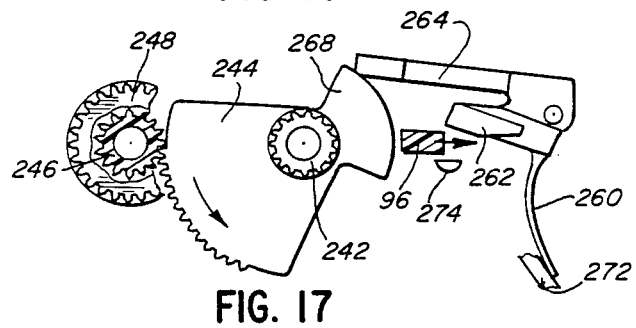
FIG. 17 is a top view of the lockout mechanism of the present invention shown partially actuated when the ram has just engaged the locking tab on the gear housing.
Figure 18:
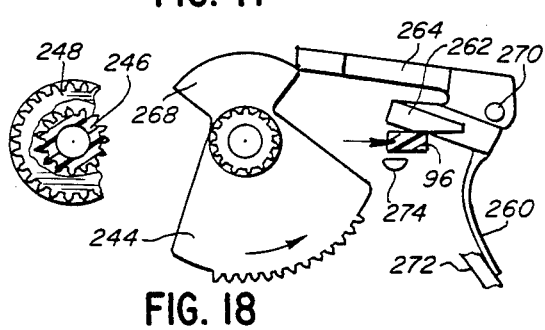
FIG. 18 is a top view of the lockout mechanism of the present invention shown partially actuated with the drawbar lug further retracted and the lockout mechanism about to disengage the camming member of the compound gear.
Figure 19:
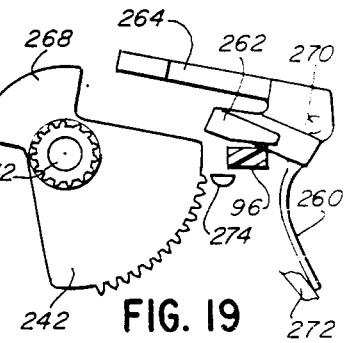
FIG. 19 is a top view of the lockout mechanism of the present invention shown with the drawbar lug preventing the lockout mechanism from returning to its unactuated position and the camming member completely disengaged from the lockout mechanism.

In an unactuated state, FIG. 15, the spring arm 260 is restrained behind a wall 272 formed in the bottom cover 70, the lockout lug 262 is positioned against a stop 274 also formed in the bottom cover and the vertical edge 276 of the distal end of the cam arm 264 is contacting the cam 268 of the compound gear 262 (FIG. 15). As the compound gear 62 rotates, the engagement with the cam arm 264 causes the lockout member 66 to rotate about the pivot 270. In the meantime, the restrained spring arm 260 is applying a counterforce. As the compound gear 62 continues to rotate, the lockout member 66 continues to rotate until the lockout lug 262, which extends upwardly through the elongate slot 104 in the chassis, has rotated into the wide portion 105 of the slot (FIG. 17). Simultaneous with the movement of the compound gear 62, the drawbar extension 52 is moving rearward. FIG. 16 shows the position of the lockout member 66 at the point in time the drawbar extension 52 is engaging the drawbar 30. As previously described, the drawbar extension 52 has a downwardly depending safety lug 96 which extends through the elongate slot 104 in the chassis 22 as well. Finally, the cam 268 on the compound gear 62 rotates out of engagement with the cam arm 264 of the lockout member 66 (FIG. 18), and the safety lug 96 has retreated to a point where it is now preventing the lockout member 66 from returning to its original position. The safety lug 96 continues to travel rearwardly and obstruct the lockout member 66 until the handles 18 are completely closed (FIG. 19).

Figure 20:
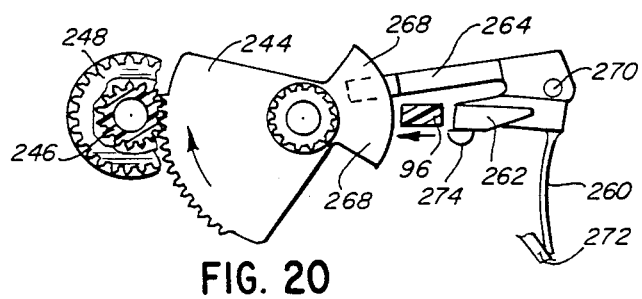
FIG. 20 is a top view of the lockout mechanism of the present invention shown in position to prevent actuation of the instrument before a clip is properly positioned in the jaws.

On the return stroke, the cam 268 on the compound gear 62 engages the opposite side 278 of the lockout member cam arm 264 which is beveled and causes the cam arm 264 to be pushed over the top of the cam 268 of the compound gear 62 (FIG. 20). At the same time, the safety lug 96 is now moving forward. Ultimately, at the point in the actuating sequence of the instrument when the forwardmost clip on the lower level 134 of the clip housing 20 is being fed to the clip load platform 26 the lockout member 66 will swing back into its original position thereby blocking the rearward movement of the safety lug 96. Consequently, if the instrument were prematurely actuated at this point, the lockout member 66 will prevent the transmission mechanism 32 from clinching the jaws and potentially deforming a clip which is not properly positioned between the jaws. Moreover, the lockout lug 262 will remain in this obstructing position until the instrument handles 18 are fully released and the next forwardmost clip is properly positioned in the jaws of the instrument. Once the handles 18 are fully opened, the compound gear cam 268 will have rotated past the cam arm 264 allowing the cam arm 264 to drop back into position. Hence, upon actuation at this point, the cam arm 264 will move the lockout lug 262 out of the way to allow the clip properly positioned in the jaws to be deformed about a blood vessel.

Whereas a preferred embodiment and certain alternative designs have been shown and described herein, it will be apparent that other modifications, alterations and variations may be made by and will occur to those skilled in the art to which this invention pertains, particularly upon considering the foregoing teachings. For example, the forward clip engaging end of the clip load spring may be comprise a center tine having only a single pair of laterally extending members interconnected by a single pair of outwardly slanted segments. A spring of this shape would also act to align the clips upon transfer to the clip load platform. In addition, it is contemplated that a clip stop may be affixed to the forward end of the tissue stop to prevent rearward movement of the clips after retraction of the ram or clip advancer. It is, therefore, contemplated by the appended claims to cover any such modifications and other embodiments as incorporated those features which constitute the essential features of this invention within the true spirit and scope of the following claims.

What is claimed is:

1. An apparatus for applying hemostatic clips comprising:

a one piece elongate chassis running the length of the apparatus for supplying structural strength to the apparatus, said chassis having a front portion and a rear portion;

a pair of opposed jaws associated with said front portion of said chassis for deforming a clip about a blood vessel;

clip housing and feed means overlying said front portion of said chassis and communicating with said jaws for storing said clips and for advancing said clips to said jaws, said clip housing and feed means including a channel shaped skirt having a bottom and two upstanding, opposed side walls, a ratchet advancer slidably supported within said skirt for supporting a plurality of the clips, a housing cover disposed in overlying relation to said ratchet advancer and attached to said skirt to create a clip storage cavity for enclosing said clips, said housing cover being provided with a ratchet surface disposed in spaced overlying relationship with said ratchet advancer, pawl means for advancing the clips through the housing, said pawl means having means for alternately engaging the ratchet advancer as the ratchet advancer moves forward such that the pawl means is moved forward with the ratchet advancer, and for engaging the ratchet surface as the ratchet advancer moves rearward to prevent rearward movement of the pawl means, and spring means for transferring the forwardmost clip from the clip housing and feed means to the clip positioning and deforming means;

clip positioning and deforming means for receiving a clip from said clip housing and feed means, advancing the clip to said jaws and deforming the clip about a vessel, said clip positioning and deforming means including a reciprocating drawbar disposed on said forward portion of said chassis and having a forward and a rearward end, said forward end defined by a pair of resilient jaw arms, said jaw arms incorporating said opposed jaws at the distal ends thereof, a resilient clip load platform subtending said jaw arms and operatively associated with said clip housing and feed means to receive the forwardmost clip from said clip housing and feed means and position the clip for advancement to said jaws, a resilient tissue stop extending from said clip load platform and subtending said jaws for preventing a vessel from forcing a clip positioned between said jaws rearwardly into the apparatus during actuation, and an elongate clip advancer reciprocably disposed between said drawbar and said front portion of said chassis for advancing individual clips to said jaws from said clip load platform; and transmission means for actuating said clip housing and feed means and said clip positioning and deforming means, said transmission means including a pair of handles pivotally connected to said rear portion of said chassis and movable between a first open position and a second closed position, a trigger spring for assisting in returning said handles to said first open position after being moved to said second closed position, a gear housing fixably mounted to said rear portion of said chassis, a reciprocating drawbar extension slideably mounted within said gear housing for engaging the rearward end of said drawbar, said drawbar extension further including an integral gear rack, a pair of links interconnecting said handles and said draw bar extension to transfer the radial movement of said handles into linear movement of said draw bar extension, a compound gear and an idler gear rotatably mounted on said gear housing and each having an upper and lower portion, said upper portion of said compound gear defining a pinion gear and engaging the rack gear of said draw bar extension, and said lower portion of said compound gear defining a gear segment for engaging and rotating said lower portion of said idler gear, said upper portion of said idler gear defining a pinion gear and engaging and reciprocating said rack gear of said ram, and a draw bar spring connected between said rearward end of said draw bar and said chassis to bias said draw bar in a forward position when said apparatus is in an unactuated position.

2. The invention of claim 1 wherein said actuation means is a pair of handle members mounted on said chassis and moveable between a first open position and a second closed position.

3. The invention of claim 1 wherein said chassis is of unitary construction.

4. The invention of claim 1 wherein said clip housing has an upper level and a lower level, said upper and lower levels adapted to hold a plurality of clips abuttingly arranged in a forward facing row, said upper level communicating with said lower level to transfer a single clip to said lower level upon movement of said actuation means from said first position to said second position.

5. The apparatus of claim 4 wherein said upper level of said clip storage cavity comprises a first ratchet surface fixably secured to said chassis, a second ratchet surface operatively coupled to said transmission means and adapted to move in a reciprocating forward and rearward motion, and pawl means for serially advancing the clips disposed between said first and second ratchet surfaces, said pawl means having engagement means for alternately engaging said second ratchet surface as said second ratchet surface moves forward such that said pawl means is moved forward with said second ratchet surface, and for engaging said first ratchet surface as said second ratchet surface moved rearward to prevent rearward movement of said pawl means.

6. The invention of claim 4 wherein said clip housing and feed means further comprises spring means associated with said clip housing for positively controlling the transfer of clips from said clip housing to said resilient clip load platform means and for centering the clip on said clip load platform to thereby allow the apparatus to be operated in any position.

7. The invention of claim 6 wherein said spring means comprises a first resilient member having a tine disposed at the forward end of said first member and defined by a pair of outwardly directed projections adapted to positively engage the legs of a clip, and a second resilient member having a tine disposed at the forward end of said second member and adapted to positively engage the crown of a clip.

8. The invention of claim 7 wherein said clip housing and feed means further comprises clip advance means for advancing a clip from said resilient clip load platform means to said jaws, said clip advance means having a first extended position between said jaws and a second retracted position substantially behind said resilient clip load platform means.

9. The invention of claim 8 wherein said clip advance means is an elongate member having a front portion shaped to engage a clip and rear portion interconnected to said transmission means and is shiftable between a first extended position wherein said front portion is located between said jaws and a retracted position wherein said front portion is remote from said jaws such that upon movement of said actuation means from said first position to said second position said transmission means causes said clip advance means to move from said first extended position to said second retracted position and upon movement of said actuation means from said second position to said first position said transmission means causes said clip advance means to move a clip from said clip load platform to a position between said jaws by moving from said second retracted position to said first extended position.

10. The invention of claim 1 further comprising a second reciprocating member interconnecting said first reciprocating member to said jaws such that during a first segment of movement of said first reciprocating member said first reciprocating member moves from a first forward position to a second intermediate position causing said clip advance means to retract from between said jaws, and during a second segment of movement said first reciprocating member engages said second reciprocating member and both move from said second intermediate position to a third rearward position causing said second reciprocating member to move said jaws rearward causing said jaws to cam close and further actuating said clip feed means to position a clip within said clip housing for advancement to said jaws, and upon return movement of said actuating means to said first position from said second position said first and second reciprocating members return to the forward most positions, said clip feed means expels a clip from said clip housing and advances said clip to a position between said jaws.

11. The invention of claim 1 further comprising a vessel stop means attached to and extending forward from said resilient clip load platform to prevent a blood vessel from forcing a clip rearward into the apparatus.

12. The invention of claim 11 wherein said vessel stop means comprises a body having a pair of outwardly extending portions to prevent said vessel stop means from becoming trapped between the spaced jaws.

13. The invention of claim 12 wherein said body is formed to provide an aperture disposed between a pair of raised shoulders to direct clips not formed about a vessel away from said apparatus.

14. The invention of claim 13 wherein said body is further provided with an upstanding rib terminating in a forward slanted front surface overlying the rear of said aperture to direct clips into said aperture.

15. The invention of claim 10 wherein said transmission means further comprises first gear means disposed on said first reciprocating member and a second gear means rotatably mounted on axle means extending through said chassis, said first gear means engaging said second gear means to impart rotary motion to said second gear means, said second gear means interconnected to said clip advance means to cause said clip advance means to reciprocate between its first extended position and its second retracted position.

16. The invention of claim 1 wherein said resilient clip load platform means comprises a pair of raised outwardly projecting platforms disposed at said distal end of said elongate forward portion of said chassis for receiving a clip from said clip housing and feed means, said clip load platform means being interconnected to said transmission means for complimentary reciprocable movement with said jaws.

17. The invention of claim 16 wherein said jaws are provided with a clip track for slidably receiving clips from said clip housing and feed means and are affixed to a pair of jaw arms interconnecting said jaws to said transmission means, said jaw arms being provided with a pair of cut out portions for nestably engaging said raised platforms to thereby align said raised platforms with said clip tracks.

18. The invention of claim 1 further comprising lockout means operatively associated with said first reciprocating member, said lockout means acting to prevent rearward movement of said first reciprocating member and thereby also preventing closure of said jaws while a clip is in transition from said clip housing to said jaws.

19. The invention of claim 18 wherein said lockout means comprises a body portion rotatably mounted on said chassis, a lockout lug extending from said body portion into the path of said first reciprocating member, camming means for causing said lockout lug to move out of the path of said first reciprocating member while said actuating means is moved from said first position to said second position, and return means to cause said lockout lug to move into the path of said first reciprocating member while a clip is in transition from said clip housing to said jaws to thereby prevent premature clip deformation.

20. In an apparatus for applying surgical clips having a pair of opposed spaced jaws, a main body including clip housing and feed means for storing and advancing clips to the jaws, and transmission means associated with the body to actuate the clip feed means and to close the jaws and deform a clip disposed therebetween, the improvement comprising: vessel stop means subtending the jaws to prevent a blood vessel from forcing a clip disposed between the jaws rearward into the body of the apparatus.

21. The invention of claim 20 wherein said vessel stop means comprises a body having a pair of outwardly extending portions to prevent said vessel stop means from becoming trapped between the spaced jaws.

22. The invention of claim 21 wherein said body is formed to provide an aperture disposed between a pair of raised shoulders to direct clips not formed about a vessel away from said apparatus.

23. The invention of claim 22 wherein said body is further provided with an upstanding rib terminating in a forward slanted front surface overlying the rear of said aperture to direct clips into said aperture.

24. In an apparatus having a pair of opposed spaced jaws for applying surgical clips, a main body including clip housing and feed means for storing and advancing clips to the jaws, actuating means mounted on the body and movable between a first and second position, and transmission means, including at least one longitudinally reciprocating member operatively associated with the jaws, the actuating means and the clip feed means to actuate the clip feed means and to cause the jaws to close to thereby deform a clip disposed therebetween upon movement of the actuating means from the first position to the second position, the improvement comprising: lockout means associated with the reciprocating member to prevent closing of the jaws when a clip is in transition from the clip housing to the jaws.

25. The invention of claim 24 wherein said lockout means comprises a body portion rotatably mounted on the apparatus, a lockout lug extending from said body portion into the path of the reciprocating member, camming means associated with the transmission means to cause said lockout lug to move out of the path of the reciprocating member while the actuating means is moved from the first position to the second position, and return means to cause said lockout lug to move into the path of the reciprocating member while a clip is in transition to the jaws.

26. In an apparatus having a pair of opposed spaced jaws, for applying surgical clips a main body including clip housing and feed means for storing and advancing clips to the jaws, and transmission means associated with the body to actuate the clip feed means and to close the jaws and deform a clip disposed therebetween, the improvement comprising: a resilient elongate member associated with the clip housing and feed means and the jaws and having clip receiving means defining a pair of raised outwardly projecting platforms and a raised central rib for positively controlling the transfer of a clip from the clip housing and feed means to the jaws.

27. The invention of claim 26 wherein said resilient elongate member further comprises vessel stop means disposed at the distal end of said elongate member and subtending said jaws to prevent a blood vessel from forcing a clip disposed between the jaws rearward into the body of the apparatus.

28. The invention of claim 27 wherein said vessel stop means comprises a body having a pair of outwardly extending portions to prevent said vessel stop means from becoming trapped between the spaced jaws.

29. The invention of claim 28 wherein said body is formed to provide an aperture disposed between a pair of raised shoulders to direct clips not formed about a vessel away from said apparatus.

30. The invention of claim 29 wherein said body is further provided with an upstanding rib terminating in a forward slanted front surface overlying the rear of said aperture to direct clips into said aperture.

31. The invention of claim 26 wherein said clip housing and feed means further comprises spring means associated with said clip housing for positively controlling the transfer of clips from said clip housing to said resilient clip load platform means and for centering the clip on said clip load platform to thereby allow the apparatus to be operated in any position.

32. The invention of claim 31 wherein said spring means comprises a first resilient member having a tine disposed at the forward end of said first member and defined by a pair of outwardly directed projections adapted to positively engage the legs of a clip and a second resilient member having a tine disposed at the forward end of said second member and adapted to positively engage the crown of a clip.

33. The invention of claim 32 wherein said outwardly directed projections extend above the jaws wherein, upon closure of the jaws, said first resilient member is caused to move upward from between the jaws.

34. In an apparatus for applying surgical clips having a pair of opposed spaced jaws, a main body including clip housing and feed means for storing and advancing clips to the jaws, and transmission means associated with the body to actuate the clip feed means and to close the jaws and deform a clip disposed therebetween, the improvement comprising: spring means comprising a resilient body having a forward tine defined by a pair of outwardly directed projections adapted to center and positively control the transfer of a clip from the clip housing and feed means to the jaws.

35. The invention of claim 34 further comprising clip load platform means associated with the clip housing and feed means and the jaws and cooperating with said spring means to positively control the transfer of a clip from the clip housing and feed means to the jaws, said clip load platform means comprising a resilient elongate member having clip receiving means defining a pair of raised outwardly directed platforms and a raised central rib for receiving a clip under the influence of said spring means.

36. The invention of claim 35 wherein the jaws are provided with a clip track for slideably receiving clips from the clip housing and feed means and are affixed to a pair of jaw arms interconnecting the jaws to the transmission means, said jaw arms provided with a pair of cut out portions for nestably engaging said raised platforms to align said raised platforms with said clip tracks.

37. An apparatus for applying surgical clips comprising a substantially rectilinear housing having a forward and a rearward end and a top member and a bottom member defining substantially open sides, a pair of handles disposed along said open sides and rotatably affixed to said forward end of said housing, said handles moveable between a first open position wherein said housing and handles are substantially V-shaped, and a second position wherein said handles are substantially incorporated into said housing, and an elongate nose portion extending from said forward end of said housing and terminating with a pair of opposed spaced jaws for deforming a clip about a blood vessel.

38. The invention of claim 37 wherein the distal ends of said handles terminate in a pair of ring grips.

39. The invention of claim 37 wherein the edges of said top and bottom members are beveled to provide a smooth transition between said housing and said handles.

40. The invention of claim 37 wherein the exterior surfaces of said handles are roughened to prevent the apparatus from slipping in the operator's hand.

41. An apparatus for applying hemostatic clips to blood vessels, arteries, veins, tissue or the like to occlude the flow of blood, said apparatus comprising:
A. a chassis running the length of the apparatus and having an elongate front portion and a rear portion;
B. a pair of opposed jaws associated with the distal end of said elongate portion of said chassis and having a clip track formed therein for receiving and deforming a clip about a vessel;
C. actuating means mounted on said rear portion of said chassis, said actuating means movable between a first position and a second position;
D. clip housing and feed means mounted to said chassis and associated with said jaws to store a plurality of hemostatic clips and to serially advance the clips one at a time to said jaws, said clip housing and feed means comprising a clip housing defining a clip storage cavity having an upper level and a lower level, said upper and lower levels adapted to hold a plurality of clips abuttingly arranged in a single forward facing row, said upper level communicating with said lower level to transfer a single clip to said lower level upon movement of said actuation means from said first position to said second position and a resilient clip load platform means subtending and communicating with said clip housing, said clip load platform means adapted to receive a single clip from said clip housing upon movement of said actuation means from said second position to said first position;
E. transmission means operatively interconnecting said jaws, said actuating means and said clip housing and feed means such that upon movement of said actuating means from said first position to said second position said jaws are caused to move rearward with respect to said chassis and be cammed closed by said chassis to deform a clip positioned between said jaws, and upon movement of said actuating means from said second position to said first position said jaws are caused to move forward with respect to said chassis and to open, and said clip housing and feed means are caused to feed a clip to said jaws.

42. The invention of claim 41 wherein said body is further provided with an upstanding rib terminating in a forward slanted front surface overlying the rear of said aperture to direct clips into said aperture.

43. An apparatus for applying hemostatic clips to blood vessels, arteries, veins, tissue or the like to occlude the flow of blood, said apparatus comprising:
A. a chassis running the length of the apparatus and having an elongate front portion and a rear portion;
B. a pair of opposed jaws associated with the distal end of said elongate portion of said chassis and having a clip track formed therein for receiving and deforming a clip about a vessel;
C. actuating means mounted on said rear portion of said chassis, said actuating means movable between a first position and a second position;
D. clip housing and feed means mounted to said chassis and associated with said jaws to store a plurality of hemostatic clips and to serially advance the clips one at a time to said jaws, said clip housing and feed means comprising a clip housing defining a clip storage cavity adapted to hold a plurality of clips abuttingly arranged in a single forward facing row, a resilient clip load platform means subtending and communicating with said clip housing, said clip load platform means adapted to receive a single clip from said clip housing upon movement of said actuating means from said second position to said first position and spring means associated with said clip housing for positively controlling the transfer of clips from said clip housing to said resilient clip load platform means and for centering the clip on said clip load platform to thereby allow the apparatus to be operated in any position;
E. transmission means operatively interconnecting said jaws, said actuating means and said clip housing and feed means such that upon movement of said actuating means from said first position to said second position said jaws are caused to move rearward with respect to said chassis and be cammed closed by said chassis to deform a clip positioned between said jaws, and upon movement of said actuating means from said second position to said first position said jaws are caused to move forward with respect to said chassis and to open, and said clip housing and feed means are caused to feed a clip to said jaws.

44. The apparatus of claim 43 wherein said upper level of said clip storage cavity comprises a first ratchet surface fixably secured to said chassis, a second ratchet surface operatively coupled to said transmission means and adapted to move in a reciprocating forward and rearward motion, and pawl means for serially advancing the clips disposed between said first and second ratchet surfaces, said pawl means having engagement means for alternately engaging said second ratchet surface as said second ratchet surface moves forward such that said pawl means is moved forward with said second ratchet surface, and for engaging said first ratchet surface as said second ratchet surface moves rearward to prevent rearward movement of said pawl means.

45. An apparatus for applying hemostatic clips to blood vessels, arteries, veins, tissue or the like to occlude the flow of blood, said apparatus comprising:
   A. a chassis running the length of the apparatus and having an elongate front portion and a rear portion;
   B. a pair of opposed jaws associated with the distal end of said elongate portion of said chassis and having a clip track formed therein for receiving and deforming a clip about a vessel;
   C. actuating means mounted on said rear portion of said chassis, said actuating means movable between a first position and a second position;
   D. clip housing and feed means mounted to said chassis and associated with said jaws to store a plurality of hemostatic clips and to serially advance the clips one at a time to said jaws, said clip housing and feed means comprising a clip housing defining a clip storage cavity adapted to hold a plurality of clips abuttingly arranged in a single forward facing row, a resilient clip load platform means subtending and communicating with said clip housing, said clip load platform means adapted to receive a single clip from said clip housing upon movement of said actuating means from said second position to said first position;
   E. transmission means operatively interconnecting said jaws, said actuating means and said clip housing and feed means such that upon movement of said actuating means from said first position to said second position said jaws are caused to move rearward with respect to said chassis and be cammed closed by said chassis to deform a clip positioned between said jaws, and upon movement of said actuating means from said second position to said first position said jaws are caused to move forward with respect to said chassis and to open, and said clip housing and feed means are caused to feed a clip to said jaws;
   F. vessel stop means attached to and extending forward from said resilient clip load platform to prevent a blood vessel from forcing a clip rearward into the apparatus, said vessel stop means comprising a body having a pair of outwardly extending portions to prevent said vessel stop means from becoming trapped between the spaced jaws.

46. The invention of claim 45 wherein said spring means comprises a first resilient member having a tine disposed at the forward end of said first member and defined by a pair of outwardly directed projections adapted to positively engage the legs of a clip, and a second resilient member having a tine disposed at the forward end of said second member and adapted to positively engage the crown of a clip.

47. In an apparatus for applying surgical clips having a pair of opposed spaced jaws, a main body including clip housing and feed means for storing and advancing clips to the jaws, and transmission means associated with the body to actuate the clip feed means and to close the jaws and deform a clip disposed therebetween, the improvement comprising: vessel stop means subtending the jaws to prevent a blood vessel from forcing a clip disposed between the jaws rearward into the body of the apparatus, said vessel stop means comprising a body having a pair of outwardly extending portions to prevent said vessel stop means from becoming trapped between the space jaws and having a pair of raised shoulders and an aperture formed therebetween to direct clips not formed about a vessel away from said apparatus.

48. The invention of claim 47 wherein said body is further provided with an upstanding rib terminating in a forward slanted front surface overlying the rear of said aperture to direct clips into said aperture.

49. An apparatus for applying hemostatic clips to blood vessels, arteries, veins, tissue or the like to occlude the flow of blood, said apparatus comprising:
   A. a chassis running the length of the apparatus and having an elongate front portion and a rear portion;
   B. a pair of opposed jaws associated with the distal end of said elongate portion of said chassis and having a clip track formed therein for receiving and deforming a clip about a vessel;
   C. actuating means mounted on said rear portion of said chassis, said actuating means movable between a first position and a second position;
   D. clip housing and feed means mounted to said chassis and associated with said jaws to serially advance the clips one at a time to said jaws, said clip housing and feed means comprising a clip housing adapted to hold a plurality of clips abuttingly arranged in a forward facing row and a resilient clip load platform means subtending and communicating with said clip housing, said clip load platform means adapted to supportingly receive a single clip from said clip housing upon movement of said actuation means from said second position to said first position;
   E. transmission means operatively interconnecting said jaws, said actuating means and said clip housing and feed means such that upon movement of said actuating means from said first position to said second position said jaws are caused to move rearward with respect to said chassis and be cammed closed by said chassis to deform a clip positioned between said jaws, and upon movement of said actuating means from said second position to said first position said jaws are caused to move forward with respect to said chassis and to open, and said clip housing and feed means are caused to feed a clip to said jaws.

50. An apparatus for applying hemostatic clips to blood vessels, arteries, veins, tissue or the like to occlude the flow of blood, said apparatus comprising:
   A. a chassis running the length of the apparatus and having an elongate front portion and a rear portion;
   B. a pair of opposed jaws associated with the distal end of said elongate portion of said chassis and having a clip track formed therein for receiving and deforming a clip about a vessel;
   C. actuating means mounted on said rear portion of said chassis, said actuating means movable between a first position and a second position;
   D. a clip housing mounted to said chassis for storing a plurality of hemostatic clips;

E. clip feed means for advancing the clips within said housing, serially expelling the clips from said clip housing and advancing the clips to the jaws; and
F. a first reciprocating member operatively interconnecting said jaws and said clip feed means to said actuating means such that, upon movement of said actuating means from said first position to said second position, said first reciprocating means moves rearward causing said jaws to move rearward with respect to said chassis and be cammed closed by said chassis to deform a clip positioned between said jaws and said feed means is positioned to advance the clips within said clip housing, and upon movement of said actuating means from said second position to said first position said first reciprocating member moves forward causing said jaws to move forward with respect to said chassis and to open, and causing said clip feed means to advance the supply of clips within said clip housing to expel the forwardmost clip from said clip housing and to position the clip between said jaws.

51. The invention of claim 8 wherein said apparatus further includes securement means operatively associated with said clip advance means and said clip advance means includes an elongate member having a front portion adapted to engage a clip and a rear portion interconnected to said transmission means, said elongate member shiftable between a first extended position wherein said front portion is located between said jaws and a retracted position wherein said rear portion engages said securement means to hold said front portion in a position remote from said jaws.

52. The invention of claim 8 or 9 further comprising securement means associated with said clip advance means for holding said clip advance means in said retracted position during closure of the jaws.

53. The invention of claim 9 or 51 wherein said securement means comprises a protuberance extending into the path of said elongate member and a receptive detent disposed on said rear portion of said elongate member such that upon movement of said elongate member to said retracted position said detent engages said protuberance and secures said elongate member in said retracted position until the clip is completely deformed.

54. In an apparatus for applying surgical clips having a pair of opposed spaced jaws, a main body including clip housing and feed means for storing and advancing clips to the jaws, and transmission means associated with the jaws and clip housing and feed means to actuate the clip feed means and to close the jaws and deform a clip disposed therebetween, the improvement comprising: securement means associated with the feed means to retain the clip feed means in a position withdrawn from the jaws while the jaws close and deform a clip.

* * * * *

UNITED STATES PATENT AND TRADEMARK OFFICE
CERTIFICATE OF CORRECTION

PATENT NO. : 4,850,355

DATED : July 25, 1989

INVENTOR(S) : CHRISTOPHER J. BROOKS, ET AL.

It is certified that error appears in the above-identified patent and that said Letters Patent is hereby corrected as shown below:

On the title page:
In the "U.S. Patent Documents", eighth reference "DIG. 10" should be --DIG. 1--

Col. 6, line 59, "vies" should be --views--

Col. 8, line 33 "or" should be --of--

Col. 9, line 21, "14" should be --41--

Col. 10, line 9 "amounts" should be --mounts--

Col. 10, line 11, following "133" insert --.  Multiple--

Col. 11, line 10, delete "or" following "134"

Col. 11, line 22, "advance" should be --advancer--

Col. 14, line 52, delete "228"

Col. 19, line 45, "moved" should be --moves--

Col. 22, line 13, delete "," following "jaws"

Col. 22, line 13, "clips" should be --clips,--

Col. 24, line 45, "actuating" should be --actuation--

Col. 25, line 30, delete "," following "row" and insert --and--

Col. 25, line 34, "actuating" should be --actuation--

UNITED STATES PATENT AND TRADEMARK OFFICE
CERTIFICATE OF CORRECTION

PATENT NO. : 4,850,355

DATED : July 25, 1989

INVENTOR(S) : CHRISTOPHER J. BROOKS, ET AL.

It is certified that error appears in the above-identified patent and that said Letters Patent is hereby corrected as shown below:

Col. 25, line 47, "are" should be --is--

Signed and Sealed this

Fifth Day of February, 1991

Attest:

HARRY F. MANBECK, JR.

Attesting Officer

Commissioner of Patents and Trademarks